United States Patent [19]
Grosz et al.

[11] Patent Number: 5,340,728
[45] Date of Patent: Aug. 23, 1994

[54] METHOD FOR AMPLIFICATION OF TARGETED SEGMENTS OF NUCLEIC ACID USING NESTED POLYMERASE CHAIN REACTION

[75] Inventors: Ron Grosz, Wilmington, Del.; Mark A. Jensen, West Chester, Pa.

[73] Assignee: E. I. Du Pont de Nemours and Company, Wilmington, Del.

[21] Appl. No.: 990,297

[22] Filed: Dec. 9, 1992

[51] Int. Cl.⁵ .................. C12P 19/34; C12Q 1/68
[52] U.S. Cl. .................. 435/91.2; 435/6; 935/17; 935/77; 536/24.32; 536/24.33
[58] Field of Search .............. 435/6, 91, 91.2; 935/77, 78, 17; 536/24.32, 24.33

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,965,188 | 10/1990 | Mullis | 435/6 |
| 5,126,239 | 6/1992 | Livak | 435/6 |

FOREIGN PATENT DOCUMENTS

| | | | |
|---|---|---|---|
| 0355989 | 2/1990 | European Pat. Off. | |
| 387696 | 9/1990 | European Pat. Off. | C12Q 1/68 |
| 409159 | 1/1991 | European Pat. Off. | C12Q 1/68 |
| 0469610 | 2/1992 | European Pat. Off. | |

OTHER PUBLICATIONS

Wu et al. DNA & Cell Biology 1991 10:233–238.
Wetmur, Crit Rev Biochem & Molec Biology, 1991 26:227–259.
Erlich et al Science (1991) 252:1643–1651.
Williams et al. Nucl Acid Res (1990) 18:6531–6535.
Simmonds et al J. Virol (1990) 64:864–872.
Lin et al J Med Virol (1992) 38:220–225.
U. Linz et al., J. Clim. Chem. Clin. Biochem. 28:5–13 (1990).
W. Rychlik et al., Nucl. Acids. Res., 18:6409–6412 (1990).
J. A. Garson et al., Lancet, 335:1419–1422 (1990).
K. Porter-Jordan et al., J. Med. Virol., 30:85–91 (1990).
E. Rimstad et al., J. Clin. Microbiol, 28(10):2275–2778 (1990).
D. Welch et al., Appl. Env. Microbiol., 56(8):2494–2498 (1990).
U. B. Gyllensten et al., Proc. Nat'. Acad. Sci., 85:7652–5656 91988).
Yourno, PCR Methods and Applications, 2:60–65 (1992).
R. J. Britten et al., Science 161(3841):529–540 (1968).
J. G. Wetmur, J. Mol. Biol. 31:349–370 (1968).
B. D. Young et al., Biochem. J. 135:573–576 (1973).
T. G. Wood et al., J. Biol. Chem., 252:457–463 (1977).
M. D. Olive, J. Clin. Microbiol., 27(2):261–265 (1989).
I. G. Wilson, Appl. Env. Microbiol. 57(6):1793–1798 (1991).
B. Furrer et al., J. Appl. Bact. 70:372–379 (1991).
C. Matsumoto et al., J. Virol, 64(11) 5290–5294 (Nov. 1990).
B. B. Plykaytis et al., J. Clin. Micro., 28(9):1913–1917 (Sep. 1990).
K. Wernars et al., J. App. Bact., 70:121–126 (1991).
K. A. Lampel., et al., Appl. Environ. Microbiol., 56:1536–1540 (Jun. 1990).
K. Wernars et al., Appl. Environ. Microbiol., 57(7):1914–1919 (Jul. 1991).
W. E. Hill et al., Appl. Environ. Microbiol., 57(3):707–711 (Mar. 1991).
U. Candrian et al., Int. J. Food Microbiol., 12(4):339–352 (1991).

*Primary Examiner*—Margaret Parr
*Assistant Examiner*—Carla Myers

[57] ABSTRACT

An improved method for performing a nested polymerase chain reaction (PCR) amplification of a targeted piece of DNA, wherein by controlling the annealing times and concentration of both the outer and the inner set of primers according to the method disclosed, highly specific and efficient amplification of a targeted piece of DNA can be achieved within one reaction vessel without depletion or removal of the outer primers from the reaction mixture vessel.

16 Claims, 25 Drawing Sheets

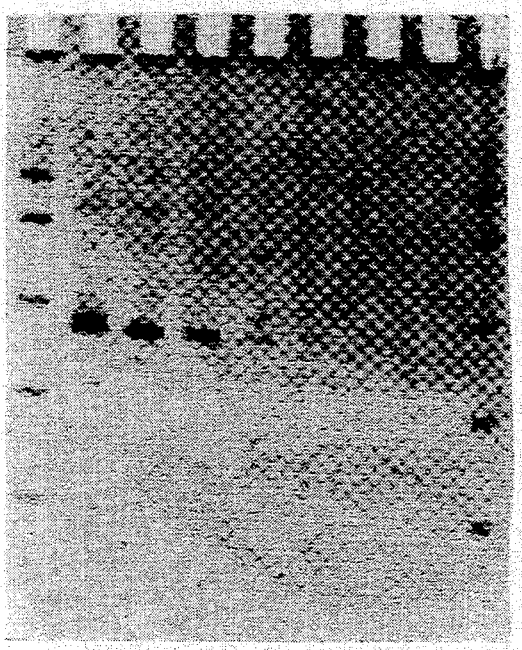 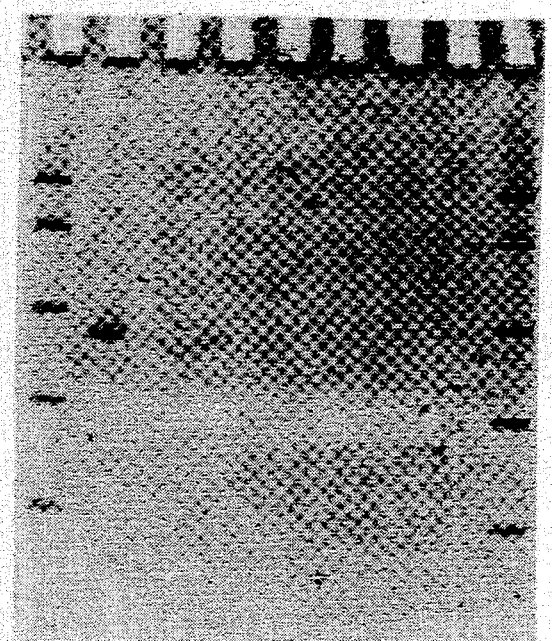

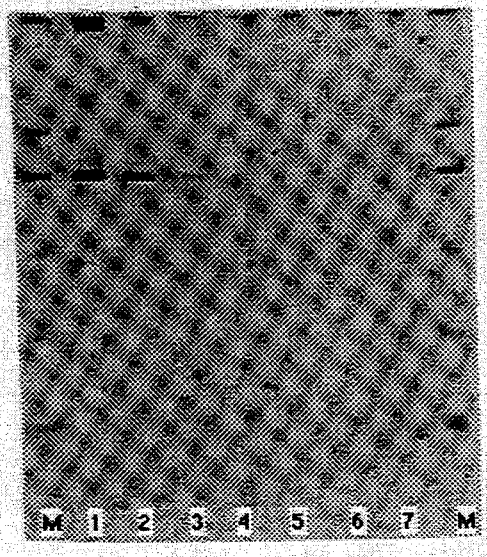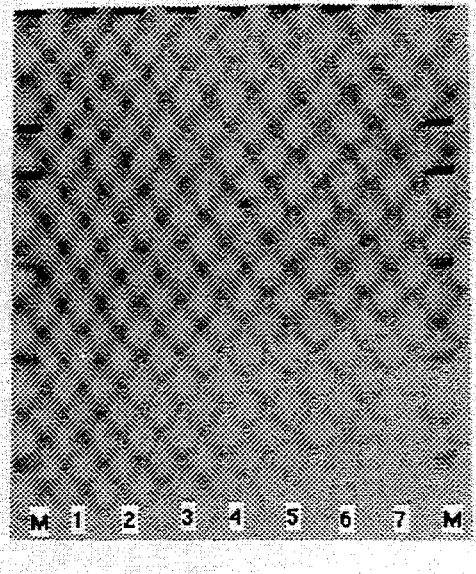

METHOD FOR AMPLIFICATION OF TARGETED SEGMENTS OF NUCLEIC ACID USING NESTED POLYMERASE CHAIN REACTION

FIELD OF THE INVENTION

This invention relates to an improved method for performing nested polymerase chain reaction amplification of a targeted segment of nucleic acid, wherein by manipulating the concentrations of the outer and inner (nested) primers and the annealing times in the first and second stages according to the method disclosed, highly specific and efficient amplification of a targeted segment of nucleic acid can be achieved within one reaction vessel. The method is characterized in that the entire quantity of outer primer is retained during the second stage of amplification without removal or primer depletion. Applicants have embodied the method in a highly sensitive assay for the rapid identification of microbial contaminants in food.

BACKGROUND OF THE INVENTION

U.S. Pat. Nos. 4,683,202 and 4,683,195 describe a process for amplifying and detecting nucleic acid sequences in a process known as the Polymerase Chain Reaction, or PCR. The PCR process consists of three basic steps: 1) denaturation of the template strands at elevated temperature; 2) annealing at hybridization temperature of oligonucleotide primers to the template DNA at the 3' ends of the sequence of interest; and 3) extension by a thermostable DNA polymerase in the presence of nucleotide triphosphates of the 3' ends of the primer to replicate the desired template sequence. Steps 1-3 are repeated in cyclic fashion so that the primer extension products of any cycle become the templates for replication in subsequent cycles and the target sequence is amplified exponentially.

U.S. Pat. No. 4,683,202 also claims a staged method of PCR in which a second set of primers is used to amplify a smaller DNA sequence contained within the DNA sequence amplified by the first primer set. The method, commonly referred to as nested PCR, is recognized as a more sensitive and specific method.

The optimization of PCR is considered in a number of publications (PCR Protocols, A Guide to Methods and Applications, Innis M. A., Gelfand, D. H., Sninsky, J. J, and White, T. J. eds., Academic, N.Y., 1990; Linz, U, Delling, U, and Rubsamen-Waigmann, H., J. Clin. Chem. Clin. Blochem., 28, 5, 1990; Rychlik, W., Spencer, W. J., and Rhoads, R. E., Nucl. Acids Res., 18, 6409, 1990; Wu, D. Y., Uggozoli, L., Pal, B. K., Qian, J, and Wallace, R. B., DNA Cell Biol., 10, 233, 1991) . Guidance is given in the selection of buffer, magnesium, nucleotide triphosphate, primer, and DNA polymerase concentrations as well as the times and temperatures employed during cycling. Particular emphasis is placed on the optimal choice of primer sequence to avoid regions of high secondary structure or complementarity between primers. Emphasis is also placed on the optimal choice of the primer annealing temperature to maximize the yield and selectivity of the amplification. However, descriptions of the influence of primer concentration and annealing time on the selectivity and yield of the amplification are not provided.

Nested PCR has been shown to increase the sensitivity of target DNA detection by at least two orders of magnitude while minimizing background from non-target DNA amplification (Garson, J. A., Tedder, R. S., Briggs, M., Tuke, P., Glazebrook, J. A., Trute, A., Parker, D., Barbara, J. A., Contreras, M., and Aloysius, S., Lancet, 335, 1419, 1990; Porter-Jordan, K., Rosenberg, E. I., Keiser, J. F., Gross, J. D., Ross, A. M., Nasim, S., and Garrett, C. T., J. Med. Virol., 30, 85, 1990). For effective nested amplification, it is necessary to terminate the amplification of the outer primer set after the first stage to allow the inner primers alone to amplify the DNA in the second stage. To minimize the carryover of outer primer into the second stage, the first stage product has traditionally been diluted (Rimstad, E., Hornes, E., Olsvik, O., and Hyllseth, B., J. Clin. Microbiol., 28, 2275, 1990) or only a small fraction (2-10%) of it is added to the second stage reaction (Welch, D., Lee, C. H., and Larsen, S. H., Appl. Env. Microbiol, 56, 2494, 1990).

Gyllensten, U. B., and Erlich, H. A., Proc. Natl. Acad. Sci., 85, 7652, 1988, describe asymmetric amplification in which one of the primers of a pair is present in one-fiftieth or one-hundredth of the usual concentration. By carrying out enough cycles, the primer present at the lower concentration will become depleted, and thus the DNA generated from the remaining primer will be selectively enriched in subsequent cycles. The primer depletion method has the disadvantage that the number of cycles required to deplete the first stage primers depends on the template DNA concentration initially present. In situations where there is an initially low sample DNA concentration the number of cycles required can be quite large (30-40), and the method is therefore not optimal for a nesting approach which depends on a lower (20-25) number of cycles per stage.

Igarashi et al., EPA Publication No. 0469610A1, claim an assay wherein a reduced primer concentration in the first stage of nested PCR gives rise to a superior target to background amplification. A reduced first stage primer concentration is an integral part of the kinetically controlled methods described in this invention. However, Igarashi's nesting protocol differs from the instant method in at least three respects. 1) The instant method demonstrates that an increased annealing time in the first stage in coordination with the reduced primer concentration is essential for high efficiency of amplification in the first stage. Igarashi operates at a constant annealing time in both stages. 2) The instant method demonstrates that the primer concentration and the annealing time must be chosen on the basis of the annealing kinetics of each primer/template combination. Igarashi does not disclose a method of arriving at optimum amplification conditions to maximize the claimed improvement. 3) Igarashi uses only 10% of the product of the first stage of amplification in the second stage, whereas the instant method utilizes the whole product of the first stage during the second stage.

Yourno, PCR Methods and Applications, 2, 60, 1992, describe a method of nested PCR in a single, closed amplification tube which is approximately 100 times more sensitive than single stage amplifications. In this method, the second stage primer and reaction mix are sequestered from the first stage amplification by entrapment in high melt agarose in a cooled portion of the tube above the temperature cycled liquid. Prior to the second stage, tubes are centrifuged to drop the agarose into the temperature cycled portion, where the agarose melts and releases the second stage reagents. Yourno also operates with a several-fold reduced first stage primer concentration. Again, this disclosure teaches constant annealing time for the first and second stages; does not give consideration to the amplification efficiency of each primer in each stage; and does not disclose any kinetic model to manipulate the amplification conditions and thereby optimally practice the nesting method.

Erlich, H. A., Gelfand, D., and Sninski, J. J., Science, 252, 1643, 1991, describe a "drop-in, drop-out" nesting in which both primer pairs are present initially and no manipulation of the reaction mixture is needed during the course of amplification, minimizing the risk of sample cross-contamination. The outer primer set is longer, or has a higher GC content than the inner set. In addition, it is implied that the extension product of the outer primer set is substantially longer or has a higher GC content than the inner primer extension product. If sufficiently high annealing and denaturation temperatures are used in the first stage, inner primer annealing is prevented while outer primer annealing, extension and denaturation proceeds. The annealing and denaturation temperatures in the second stage are reduced to enable inner primer annealing and to prevent outer primer extension product denaturation. The inner primers are thus "dropped in" in the second stage by proceeding with a reduced annealing temperature, and outer primer amplification is a "dropped out" by the lower denaturation temperature. Alternatively, the outer primers can be "dropped out" by depleting them in the first stage in a manner analogous to asymmetric amplification. The general applicability and effectiveness of "dropping out" primers by reduced denaturation temperature is not disclosed.

The kinetics of annealing oligonucleotide probes to DNA and the reannealing of denatured strands of genomic DNA have been studied (Britten, R. J. and Kohne, D. E., Science, 161, 529, 1968, Wetmur, J. G., J Molec. Biol., 31, 329, 1968, Young, B. D. and Paul J., Blochem J., 135, 573, 1973) and described as second order. Such rate modelling has contemplated hybridization efficiency as a function of DNA concentration and contact time in studies involving affinity capture for detection purposes (Wood, T. G., and Lingrel, J. B., J. Biol. Chem., 252, 457, 1977; and Mc Mahon, M. E., European Patent Application 90104413.1). However, primer annealing kinetics has not been a variable which has been recognized in the design and control of gene amplification by PCR.

The present invention is a method to perform nested PCR in which the entire product of the first stage of nesting is used in the second stage without the need to dilute, deplete, or otherwise remove the outer primers. Applicants have achieved efficient selective amplification of the outer primers in the first stage, and their dropout in the second stage, solely by controlling the rate of primer annealing to the template at each stage. The annealing kinetics have been manipulated by carefully selecting and controlling primer concentrations and annealing times in the first and second stages according to predictions of Applicants' second order kinetic model wherein the parameters are evaluated independently for each primer pair and template.

Applicants' kinetically controlled method of dropping out the outer primers is distinct and advantageous over the existing art in that 1) primer annealing temperature need not be varied throughout the nesting stages; 2) the second stage can be activated after any desired number of cycles; and 3) the method is independent of the starting nucleic acid concentration and also of the relative sizes of the primer extension products. The method can be practiced within one reaction vessel.

Although it is contemplated that Applicants' abovedescribed nested amplification method may be utilized in any procedure wherein specific segments of nucleic acids are replicated for analytical, diagnostic or genetic cloning purposes, the invention has been embodied in the instant application in a highly sensitive method for the identification of microbial contaminants in food. Specifically, Applicants' food diagnostic methodology entails in the first step, identifying a random, unique segment of DNA for each individual microorganism of interest which will be diagnostic for that microorganism. To identify and obtain this diagnostic nucleic acid segment, a series of polymorphic markers is generated from each organism of interest using single primer RAPD (Random Amplified Polymorphic DNA) analyses as described in Nucleic Acid Research, Vol. 18, No. 22, pp. 6531–35, Williams et al., and U.S. Pat. No. 5,126,239 (1992), E. I. du Pont de Nemours and Company. The RAPD series from each organism is compared to similarly-generated RAPD series from other organisms, and a RAPD marker unique to each organism of interest is selected. The unique markers are then isolated, amplified and sequenced. Outer primers and inner primers for each marker may then be developed. These primers will comprise sequence segments within the RAPD marker, and the inner set of primers will be complementary to the 3' ends of the target piece of nucleic acid. These outer and inner nested primers may then be used in Applicants' improved nested PCR amplification method, on food samples for example, to enable the highly sensitive, rapid and precise identification of microbial contaminants.

Other methods are known which utilize nested PCR techniques for the identification of microbial food contaminants. However, none of these methods employ Applicants' improved nested PCR which accomplishes highly efficient amplification of the diagnostic nucleic acid target by manipulation of primer concentration and annealing times at each stage of amplification. (Olive, M. D., J. Clin. Microbiol., 27, 261, 1989; Wilson, I. G., Cooper, J. E. and Gilmour, A., Appl. Env. Microbiol., 57, 1793, 1991; Furrer, B., Candrian, U., Hoefelein, C., and Luethy, J., J. Appl. Bact., 70, 372, 1991).

SUMMARY OF THE INVENTION

Applicants have provided an improved method for performing a nested polymerase chain reaction to selectively amplify a target segment of nucleic acid from a sample nucleic acid reaction mixture. The method amplifies in the first stage a nucleic acid segment which is flanked by an outer primer pair, and in the second stage amplifies a nucleic acid target segment which is flanked by an inner, or nested primer pair. The improvement comprises a method of controlling the concentrations and annealing times of the outer and inner primers in the first and second stages whereby selective amplification of a target segment of nucleic acid is accomplished during the second stage. The method is characterized in that the entire volume of the first stage reaction mixture is used in the second stage without depletion or removal of the outer primers from the reaction mixture. The improved method comprises the steps of:

adding the pair of outer primers to the nucleic acid reaction mixture to achieve a concentration of said outer primers which is described by $P_{o11}$;

repetitively performing the polymerase chain reaction utilizing an annealing time at each cycle which is described by $t_1$;

adding the pair of inner (nested) primers to the nucleic acid reaction mixture to achieve a concentration of said inner primer which is described by $P_{022}$; and repetitively performing the polymerase chain reaction utilizing an annealing time at each cycle which is described by t2;

wherein $P_{011}$, $t_1$, $P_{022}$ and $t_2$ are selected according to the formulas $$\epsilon_{max\,1}(1-\exp-(k_1 P_{011} t_1)) > 0.4$$
$$\epsilon_{max\,2}(1-\exp-(k_2 P_{022} t_2)) > 0.4$$
$$\epsilon_{max\,1}(1-\exp(-k_1 P_{012} t_2)) < 1/5 \; \epsilon_{max\,2}(1-\exp(-k_2 P_{022} t_2))$$

wherein $P_{011}$ is the concentration of each of the outer primers in the first stage;

$P_{022}$ is the concentration of each of the inner primers in the second stage;

$P_{012}$ is the concentration of each of the outer primers in the second stage;

$t_1$ is the annealing time in the first stage;

$t_2$ is the annealing time in the second stage;

$k_1$ is the second order rate constant for the formation of extension product from the outer primers;

$k_2$ is the second order rate constant for the formation of extension product from the inner primers;

$\epsilon_{max\,1}$ is the maximum per cycle primer extension of the outer primer; and $\epsilon_{max\,2}$ is the maximum per cycle extension of the inner primers.

BRIEF DESCRIPTION OF THE DRAWINGS

FIGS. 3A-3J compares the amplification of the *Salmonella typhimurium* DNA with primers 33-17-3 and 33-17-6 (Table 2) at various primer concentrations and annealing times. The same samples as in FIG. 1 were used.

FIGS. 7A-7J compares the amplification of the *E. coli* DNA with primers 15-A2 and 15-L (Table 2) at various primer concentrations and annealing times. Samples 1-6 are serial 10-fold dilutions of the DNA, the highest concentration sample being $2 \times 10^9$ copies of genomic DNA per milliliter, based on viable cell counts. Sample 7 is a control with no *E. coli* DNA.

DETAILED DESCRIPTION

Figure 1A:
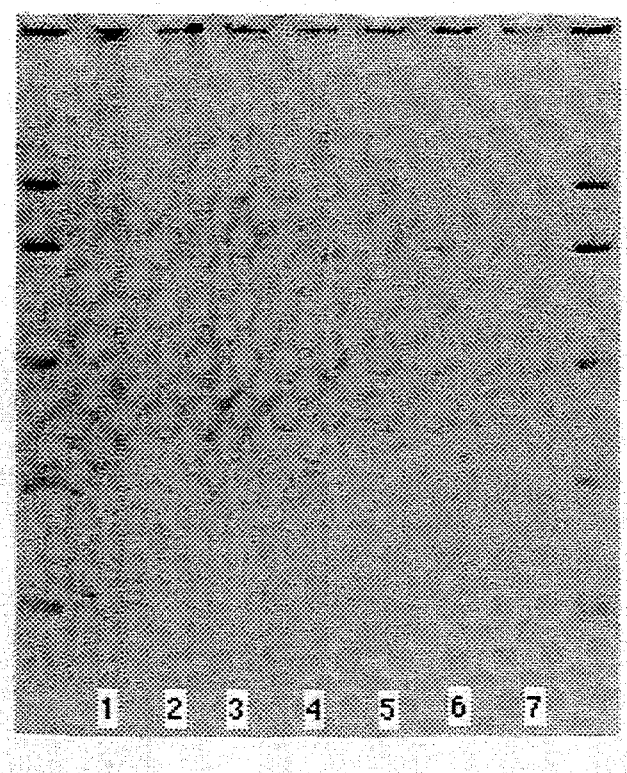
FIG. 1 compares 10 (FIG. 1A) and 28 (FIG. 1B) cycle PCR amplifications of *Salmonella typhimurium* DNA, using primers 33-17-6 and 33-17-3 (Table 2). Samples 1-6 are serial 10-fold dilutions of the DNA, the highest concentration sample being $5 \times 10^8$ copies of genomic DNA per milliliter, based on viable cell counts. Sample 7 is a control with no Salmonella DNA.

The following terms are intended to convey the meanings set forth below for purposes of this application.

A "nested polymerase chain reaction" refers to a staged polymerase chain reaction process in which a pair of "outer" primers which flank a particular first segment of nucleic acid are used to amplify that first segment in stage 1; and then in stage 2 a second set of "inner" or "nested" primers is used to amplify a smaller "target" segment of nucleic acid which is contained within the first segment. The nested or inner primers will flank that target nucleic acid. "Flanking primers" is used to describe primers which are complementary to segments on the 3' end portions of the double-stranded nucleic acid segment which is polymerized and amplified during the PCR process. The polymerase chain reaction (PCR) and the nested PCR method are disclosed in U.S. Pat. No. 4,683,202, which is hereby incorporated by reference. Although Applicants have embodied the instant improved nested PCR method using two primer pairs and two stages of nesting, the instant method is equally applicable wherein three or even more stages of nesting are employed. More than two stages of nesting could become important if additional selectivity in the amplification of target over background is required. Also, the instant nested PCR method has been embodied wherein the inner nested primer set is added to the reaction mixture after the completion of the first stage of nesting. Applicants' method of achieving selective and highly efficient, kinetically controlled nested amplification can also be practiced, however, wherein both sets of primers are added to the reaction mixture prior to the first stage of the reaction and no reagents are added or removed from the mixture after the initiation of temperature cycling. This "kinetically controlled uninterrupted" nesting method can be practiced in a manner similar to the "drop-in drop-out" nesting method described in the art in that the amplification reaction tubes need not be opened during the amplification, minimizing the chance of sample cross-contamination. Applicants' "kinetically controlled uninterrupted" nesting differs from "drop-in drop-out nesting" in that activation or deactivation of primer pairs is achieved by manipulating primer concentrations and annealing times according to the instant kinetic model, and not by primer depletion or variation of the denaturing temperature.

As an example of uninterrupted kinetically controlled nesting, one could practice the method embodied herein with the following modifications. 1) The outer primers must be longer or have a higher GC content than the inner set. 2) The annealing temperature in the first stage must be sufficiently high that the outer primer anneals efficiently but the inner primers do not. 3) The annealing temperature in the second stage must be sufficiently low such that the inner primer pair can anneal efficiently. 4) The kinetic parameters $\epsilon_{max\,1}$, $k_1$, $\epsilon_{max\,2}$ and $k_2$ must be evaluated at the two annealing temperatures. And 5) the time that the temperature cycler spends between the first stage annealing temperature and the second stage annealing temperature in the second stage must be added to the annealing time in all kinetic terms applying to the outer primer. The governing equations of "kinetically controlled uninterrupted nesting" become:

$\epsilon_{max1}(T_1)(1-\exp-(k_1(T_1)P_{01}t_1)) > 0.4$ $\epsilon_{max2}(T_2)(1-\exp-(k_2(T_2)P_{02}t_2)) > 0.4$ $\epsilon_{max1}(T_2)(1-\exp-(k_1(T_2)P_{01}(t_2+\Delta t))) < 1/5 \cdot \epsilon_{max2}(T_2)(1-\exp-(k_2(T_2)P_{02}t_2))$ Where:
$P_{01}$ is the outer primer concentration;
$P_{02}$ is the inner (nested) primer concentration;
$T_1$ is the first stage annealing temperature;
$T_2$ is the second stage annealing temperature;
$k_1(T_1), k_1(T_2), \epsilon_{max1}(T_1), \epsilon_{max1}(T_2), \epsilon_{max2}(T_2), k_2(T_2)$ are the annealing kinetic parameters evaluated at the given annealing temperatures; $\Delta t$ is the time the temperature cycler spends between the two annealing temperatures in the second stage.

In this modified method, the inner primers are introduced prior to the second stage by dropping the annealing temperature rather than by physically adding them.

By "amplify" or "selectively amplify" Applicants mean an increase by at least a factor of 100 of the target sequence of nucleic acid and an enrichment by at least a factor of 100 of the target DNA concentration relative to the background DNA concentration.

By "sample nucleic acid mixture" Applicants mean a sample containing nucleic acids and mixtures thereof from any individual, strain, species or genera of organisms; including nucleic acids derived from any living source including any plants, animals, yeasts, microorganisms, or viral organisms, or any portions thereof which contain nucleic acid. For example, the method is applicable to amplifying a segment of DNA of the genome in the genus Salmonella which is contained in a sample comprising *Salmonella typhimurium* and DNA from beef. Other examples include the detection of sequences contained within the species *Listeria monocytogenes*, or the genus Listeria, or the species *Staphylococcus aureus*, or the species *E. coli*, or the subspecies of enterotoxic *E. coli*, in samples containing beverages, foods, and other microorganisms. The instant invention is also especially suitable for amplifying nucleic acids from environmental samples to detect the presence of microbial organisms which might be present therein; for example, from water, soil or vegetative samples. The instant invention is applicable as well for amplification of nucleic acids, for diagnostic or forensic purposes, from biological samples containing prokaryotic, eukoryotic, or viral cells. Typical examples of these types of biological sources includes human or animal samples containing blood, urine, tissue, semen, bacterial and hair.

Kinetic Model

A mathematical model has been developed (Equation 1) which approximates a description of the annealing kinetics in PCR. The hybridization of the primers to template DNA strands is modelled as a second order kinetic process. Second order kinetics has accurately described annealing of RNA or DNA probes to single stranded DNA, and the reannealing of denatured, double stranded DNA (Young, B. D. and Paul, J., Biochem J., 135, 573, 1973 and Britten, R. J., and Kohne, D. E., Science, 161, 529, 1968). Thus, the annealing rate is given by:

$$\frac{d(H)}{dt} = k(D)(P) \qquad (1)$$

where H is the concentration of primer hybridized to the DNA template, D is the concentration of unhybridized template, P is the concentration of unhybridized primer, t is time, and k is the second order rate constant. In PCR reactions, this representation is an approximation since there are two primers annealing to opposite strands. Thus, for PCR the overall annealing rate expressed in Equation 1 can be considered as either a composite of the two primer annealing rates or as the slower of the two annealing rates.

The hybridization process is initiated in PCR after the denaturation step upon the attainment of the annealing temperature. Thus, the initial state is expressed as:

$$\text{at } t=0, H=0 \qquad (2)$$

Certain methods of nested PCR require the depletion of the outer primer pair (Erlich, H. A., Gelfand, D., and Sninsky, J. J., Science, 252, 1643, 1991). In contrast, the instant method works best without outer primer depletion, and with the transition to the second stage of nested amplification while the outer primer copy number greatly exceeds the copy number of the extension product. Thus, during the instant kinetic control method the primers are in excess. As a result, the primer concentration in Equation 1 can be considered a constant equal to the initial primer concentration added at the start to the amplification reaction. Hence, $P = P_0$. Finally, the sum of the concentrations of hybridized and unhybridized template equals the total template DNA concentration at the start of the annealing segment of the cycle:

$$H + D = D_0 \tag{3}$$

Solving the Equations and initial conditions 1-3 gives:

$$H/D_0 = \alpha = (1 - \exp(-k\, P_0 t)) \tag{4}$$

Equation 4 states that the concentration of primer hybridized to template starts at zero and asymptotically approaches the total template DNA concentration as the time t increases in the annealing segment of the cycle. The rate of approach to complete hybridization is governed by one intrinsic parameter, k, which differs for different primer sequence, primer length, annealing temperature, salt concentration, and origin of the template DNA. The sole control variable is $P_0 t$, the product of the primer concentration and the annealing time. It should be evident that different combinations of primer concentration and annealing time can achieve the same result as long as the product of the variable combinations is equal.

It is assumed that during the kinetic control recommended in this invention, the rate limiting step of the PCR process is the rate of annealing of primer to template. That is, it is assumed the Taq polymerase enzyme (or other polymerization enzyme) has sufficient activity within the reaction mixture to completely extend all primers that are annealed to the template. This assumption breaks down during the very last stages of amplification where the products reach high concentration. However, in practical terms this late time period can be disregarded in design of the instant kinetically controlled nested process. Given this assumption, the total extent of amplification over N cycles of PCR is therefore given by:

$$A = (1 + \alpha)^N \tag{5}$$

where A is the degree of amplification defined as the molar concentration of extension product at the end of PCR divided by the molar concentration of template DNA initially present. DNA concentrations expressed in copies/ml also yield the same value of A. Equation 5 simply states that all annealed primer is extended in each cycle of the amplification, and the final amplification is a composite of the extension products made in each cycle. The extension products of cycle N become the templates of cycle N+1.

One final addition to equation 5 improves the fit of the model to real data:

$$A = (1 + E)^N \tag{6}$$

$$E = \epsilon_{max} \alpha$$

where $\epsilon_{max}$ represents a maximum per cycle efficiency whose value is between zero and one. The fraction of template molecules that give rise to extension products in one cycle cannot exceed the fraction $\epsilon_{max}$. No physical interpretation of this limit is needed for effective use of this model.

According to the suggested model, once the parameter values $\epsilon_{max}$ and k are known for a given primer/template system, the amplification efficiency per cycle and over any number N of cycles can be predicted from the primer concentration and the annealing time. With this predictive ability, one can optimally choose outer and inner nested primer concentrations and the annealing times in each stage to be used in the nesting method of this invention.

Wu et al. (Wu, D. Y., Ugozzoli, L., Pal, B. K., Quian, J., and Wallace, R. B., DNA Cell Biol., 10, 233, 1991) have observed that the optimal annealing temperature for PCR is above the melting temperature of the primer and its complimentary oligonucleotide. They suggest that the primer does not completely anneal to the template during PCR, but rather, it approaches the template in an orientation sufficient for the enzyme to extend its 3' end. The primer extension product has a melting temperature greater than the annealing temperature, and hybridization is completed at that point. The model of equations 4 and 6 can account for the mechanism proposed by Wu et al. It is only necessary to redefine H as the fraction of primer molecules which approach the templates in an orientation enabling their extension by Taq polymerase. It is still assumed that the rate limiting step of the process is the kinetics of primer/template interaction and that the kinetics is second order.

Evaluation of Kinetic Parameters

The kinetic parameters k and $\epsilon_{max}$ are known to have different values for different primers, templates, and annealing conditions. The following discussion explains a preferred mode of evaluating model parameters from experimental data in any particular system. Again, other models and parameter evaluation methods can be used, even trial and error, to adjust the nesting parameters for the practice of this invention.

First, the total amplification factor A must be measured experimentally. DNA concentrations can be measured by a variety of known techniques such as radiolabelling; the template DNA can be made radioactive, and radiolabelled primer or nucleotide triphosphates can be incorporated into the amplification buffer. In addition, concentrations can be measured by separation of DNA by gel electrophoresis, staining, and densitometry, or UV absorbance of purified DNA. Finally, if the template DNA is derived from the genome of viable organisms, the DNA concentration can be estimated by colony counts on agar spread plates.

The amplification factor A is measured as a function of an increasing product of the primer concentration and annealing time. The model of equations 4 and 6 are optimally fit to the data to obtain estimates of the parameters k and $\epsilon_{max}$.

Application of the Kinetic Model in the Process of the Invention

This invention is an improved method of performing nested polymerase chain reaction wherein three parameters of the nesting method are constrained: 1) the primer extension products of the first stage of nesting are efficiently formed from the outer primer set; 2) the primer extension products of the second stage of nesting are formed predominantly from the inner primer set; and 3) the primer extension products of the second stage of nesting are formed efficiently from the inner primer set. Efficiency is defined such that in each amplification cycle extension products are made from at least 40% of the template DNA present at the start of the cycle from the designated primers. Predominance is defined such that in each cycle of the second stage, at least 5 times as much extension product is made from the inner primer set than the outer set. Additional characteristics of the embodiment described are: 4) the entire product of the first stage of nesting is used in the second stage without effective dilution and without outer primer removal or depletion; 5) the same annealing temperature may be maintained during both stages of nesting; and 6) the inner or nested primers are absent in the first stage of nesting and are added to the product of the first stage.

Satisfaction of the first 3 parameters of this invention requires the ability to kinetically control: 1) the extent of outer primer extension in the first stage so that greater than 40% of the DNA templates are extended in each cycle; 2) the extent of inner primer extension in the second stage so that greater than 40% of the DNA templates are extended in each cycle; and 3) the extent of inner and outer primer extensions in the second stage so that in each cycle, at least 5 times more inner primer extension products are formed than outer primer products.

To state the constraints mathematically, we have defined $E_{ij}$ (Equation 6) to be the per cycle fraction of the DNA template that is extended by primer set i in nesting stage j. Primer set 1 is the outer set, and primer set 2 is the inner set. Then, the constraints are: 1) $E_{11} > 0.4$; 2) $E_{22} > 0.4$; and 3) $E_{12} < 1/5\ E_{22}$. To accomplish this, some level of understanding of the rate limiting kinetics of primer extension is necessary in order to interrelate primer extension with other reaction variables such as primer concentration, annealing time, annealing temperature, Taq polymerase activity, NTP (nucleotide triphosphate) concentration, Mg concentration, pH, buffer composition, extension time, extension temperature, etc. According to Applicants' second order kinetic model, at a given annealing temperature, the extent of primer extension, E, will be determined solely by the mathematical product of the primer concentration and the annealing time, designated $P_0t$. Furthermore, E increases with increasing $P_0 t$ at a progressively decreasing slope, and approaches a maximum extent of primer extension. The rate at which E asymptotically approaches its maximum value, $\epsilon_{max}$, with increasing $P_0t$ is governed by the second order rate constant k. The relationship between the E, P0 and t is given in model equations 4 and 6:

$$E = \epsilon_{max}(1 - \exp-(kP_0t))$$

The value of k is characteristic of each primer/template system at a given annealing temperature and polymerase buffer and varies with changing temperature and buffer composition.

With the model, the constraints can be imposed in terms of physical control variable such as primer concentration and annealing time. Some new parameters need to be defined: $k_i$ is the second order rate constant k for annealing of primer set i; $\epsilon_{max\ i}$ is the maximum per cycle extension efficiency of primer set i; $P_{0ij}$ is the concentration of primer set i in stage j; and $t_i$ is the annealing time of stage i.

The inequality constraints of the nested amplification become:

$$\epsilon_{max\ 1}(1 - \exp-(k_1P_{011}t_1)) > 0.4 \qquad (9)$$

$$\epsilon_{max\ 2}(1 - \exp-(k_2P_{022}t_2)) > 0.4 \qquad (10)$$

$$\epsilon_{max\ 1}(1 - \exp(-k_1P_{012}t_2)) < 1/5\ \epsilon_{max\ 2}(1 - \exp(-k_2P_{022}t_2)) \qquad (11)$$

$P_{011}$, the outer primer concentration in the first stage, differs from $P_{012}$, the outer primer concentration in the second stage, only because inner primer set (along with additional buffer, NTP's, magnesium, etc.) is added to the product of the first stage of amplification prior to the second stage. Stated mathematically, $P_{011}/P_{012} = V_2/V_1$ where $V_1$ and $V_2$ are the total reaction volumes in the first stage and the second stage. Typically, $V_2/V_1$ is chosen to be between 1 and 4, and more typically between 2 and 4.

To practice the invention, it is necessary to evaluate the parameters $\epsilon_{max}$ and k for both primer sets and to choose primer concentrations, annealing times, and the volumes of the first and second stage reagent mixes so that these constraints are fulfilled.

Usually $\epsilon_{max\ 1}$ and $\epsilon_{max\ 2}$ are roughly equal between 0.8 and 0.9, and, typically, $(1 - \exp-(k_1P_{011}t_1))$ is chosen to be between 0.7 and 0.9 and $(1 - \exp-(K_2P_{022}t_2))$ is chosen to be greater than 0.7. ($k_1P_{011}t_1$ between 1.2 and 2.3 and $k_2P_{022}t_2$ greater than 1.2). Therefore, the left hand sides of equations 9 and 10 are often between 0.55 and 0.8 and greater than 0.55, respectively. With these constraints, $k_1P_{012}$ must be less than $k_2P_{022}$ by at least a factor of 8 to satisfy equation 11. Most often, $k_2P_{022}$ is chosen to exceed $k_1P_{012}$ by at least a factor of 15-20. Second order rate constants k have been observed to vary between nested primer sets by less than a factor of four, and typically, by less than a factor of two. This implies that in the second stage, the inner primers are usually present in a concentration 8 to 40 times higher than the outer primers.

$15 < k_2P_{022}/k_1P_{012}$ implies that $15 < V_2k_2P_{022}/V_1k_1P_{011}$. In addition, since $(k_1P_{011}t_1)$ (between 1.2 and 2.3) is usually less than or equal to $(k_2P_{022}t_2)$ (greater than 1.2) the latter inequality would be satisfied if $15 < V_2t_1/V_1t_2$. The last inequality states that in the typical case, the first stage annealing time is longer than the second stage annealing time by a factor that depends on the volume ratio of the first and second stages. For example, for $V_2/V_1 = 2$, the annealing time of the first stage should be at least 7 times longer than in the second stage.

In summary, the general constraints of the invention, equations 9–11, have been simplified and generalized for the more typical cases to be:

$$1.2 < k_1P_{011}t_1 < 2.3 \qquad (12)$$

$$1.2 < k_2P_{022}t_2 \qquad (13)$$

$$15 < V_2t_1/V_1t_2 \qquad (14)$$

$$2 < V_2/V_1 < 4 \qquad (15)$$

A convenient method to design the nesting strategy of this invention is to choose the first stage annealing time to be around $16V_1/V_2$ minutes. The outer primer concentration in the first stage is then obtained by solving equation 12. The second stage annealing time is then calculated using 14. Finally, the inner primer concentration in the second stage is obtained from equation 13.

In a less desirable but still feasible method of practicing this invention, the primer concentrations and annealing times are determined by trial and error without the systematic evaluation of the kinetic parameters k and $\epsilon_{max}$. Initial estimates could be made by referring to kinetic parameters of other primer/template systems. Applying typical values of k of 10 to 40 $\mu$M Min to the rules of thumb of Equations 12-14, the following parameters are provided for the generalized practice of the instant invention:

For $1<V_2/V_1<2$: (16)

$t_1 = 6.5$ to 13 min
$P_{011} = 0.0015$–$0.03$ $\mu M$
$t_2 = 0.5$–$1.6$ min
$P_{022} = 0.1$–$1$ $\mu M$ For $2<V_2/V_1<3$: (17)

$t_1 = 4$ to 9 min
$P_{011} = 0.0025$–$0.05$ $\mu M$
$t_2 = 0.5$–$1.6$ min
$P_{022} = 0.1$–$1$ $\mu M$ For $3<V_2/V_1<4$: (18)

$t_1 = 2.5$ to 6.5 min
$P_{011} = 0.0035$–$0.07$ $\mu M$
$t_2 = 0.5$–$1.6$ min
$P_{022} = 0.1$–$1$ $\mu M$ The parameters can be estimated accordingly for other values of $V_2/V_1$.

Embodiment of the Method to Detect Microbes

In a preferred embodiment of Applicants' invention, the improved nesting PCR method is practiced to detect specific DNA segments from a sample reaction mixture containing DNA from unknown food contaminating microorganisms. By the detection of amplified DNA segments from this mixture which are known to be unique to a particular microbe, the presence of that microbe in the sample mixture can be determined.

A method based upon screening with arbitrary primers has been developed to select unique segments of DNA which will be diagnostic for a specified microorganism at the genus, species, serotype or strain level.

Selection of Arbitrary Primers

Four 12-base primers of arbitrary composition were formulated for the purpose of sampling the genomes of target microorganisms by means of DNA amplification reactions. Single primers were used in amplification reactions which generated a characteristic pattern of products from the microbial genomic DNA. The polymorphisms identified in these patterns are called Random Amplified Polymorphic DNA (RAPD) markers and are described by Williams et al., in Nucleic Acid Research, Vol. 18, No. 22, pp. 6531-6535. The primers had arbitrary sequences which meet the following criteria:

1) no sequence matches between primers of >4 bases,
2) no repeats of single or double base sequence of >2, for example:
   i) GG would be allowed, GGG would not
   ii) CTCT would be allowed, CTCTCT would not
3) no reverse complementary sequence within a primer of >4 bases, and
4) G+C composition of the primers would be 50%.

The purpose of these criteria were 4-fold:

1) to insure a broad sampling of the microorganism genome;
2) to minimize degenerate amplification of highly repeated sequences;
3) to minimize primer-dimer amplifications; and
4) to insure that all the primers could be used under identical amplification conditions.

The primer sequences were selected as follows:

5'd(AGC TGA TGC TAC)3' CN01 SEQ ID NO:1
5'd(AGT CGA ACT GTC)3' CN02 SEQ ID NO:2
5'd(TTA GTC ACG GCA)3' CN03 SEQ ID NO:3
5'd(TGC GAT ACC GTA)3' CN04 SEQ ID NO:4

To increase the range of possible amplification sites a second series of four 12-base primers were subsequently prepared.

5'd(CTA CAG CTG ATG)3' CN05 SEQ ID NO:5
5'd(GTC AGT CGA ACT)3' CN06 SEQ ID NO:6
5'd(GGC ATT AGT CAC)3' CN07 SEQ ID NO:7
5'd(CGT ATG CGA TAC)3' CN08 SEQ ID NO:8

The sequences of CN05-08 were derived from CN01-04, respectively. They were generated by taking the last 3-4 bases from the 3' end of the primer and transposing them to the 5' end.

Selection of Microbial Test Panel

A microbial test panel comprising a variety of Salmonella serotypes and bacteria of related genera which are difficult to differentiate from Salmonella using classical identification techniques was complied. The composition of the test panels is shown in Table 1.

TABLE 1

| Salmonella and Non-Salmonella Test Panel Compositions | |
|---|---|
| Salmonella | Strain No. |
| 1. S. typhimurium | 586 |
| 2. S. enteritidis | 590 |
| 3. S. typhimuruim | 731 |
| 4. S. typhi | 584 |
| 5. S. typhi | 585 |
| 6. S. typhimurium | 587 |
| 7. S. typhimurium | 588 |
| 8. S. typhimurium | 589 |
| 9. S. typhimurium | 708 |
| 10. S. saintpaul | 1086 |
| 11. S. binza | 1085 |
| 12. S. napoli | 966 |
| 13. S. enteritidis | 1109 |
| 14. S. enteritidis | 737 |
| 15. S. enteritidis | 890 |
| 16. S. enteritidis | 903 |
| 17. S. clerkenwell | 965 |
| 18. S. infantis | 732 |
| 19. S. infantis | 900 |
| 20. S. infantis | 908 |
| 21. S. newport | 707 |
| 22. S. arizona | 725 |
| 23. S. sp. | 728 |
| 24. S. heidelberg | 577 |
| 25. S. virchow | 738 |
| 26. S. stanley | 739 |
| 27. S. senftenberg | 740 |
| 28. S. gallinarium | 741 |
| 29. S. colerasuis | 917 |
| 30. S. paratyphi | 918 |
| 31. S. solt | 963 |
| 32. S. bredeney | 964 |
| Non-Salmonella | Strain No. |
| 1. Shigella sonnei | 702 |
| 2. Shigella flexneri | 1083 |
| 3. Shigella dysenteria | 1082 |
| 4. Shigella boydii | 1081 |
| 5. Citrobacter diversus | 97 |
| 6. Citrobacter diversus | 217 |
| 7. Citrobacter diversus | 227 |
| 8. Citrobacter diversus | 378 |
| 9. Citrobacter freundii | 226 |
| 10. Citrobacter freundii | 267 |
| 11. Citrobacter freundii | 355 |
| 12. Citrobacter freundii | 361 |
| 13. Citrobacter freundii | 370 |

TABLE 1-continued

Salmonella and Non-Salmonella Test Panel Compositions

| | | |
|---|---|---|
| 14. | *Citrobacter freundii* | 383 |
| 15. | *Citrobacter freundii* | 330 |
| 16. | *Citrobacter freundii* | 341 |
| 17. | *E. coli* | 84 |
| 18. | *E. coli* | 154 |
| 19. | *E. coli* | 282 |
| 20. | *E. coli* | 703 |
| 21. | *E. coli* | 925 |
| 22. | *E. coli* | 885 |
| 23. | *E. coli* | 53 |
| 24. | *E. coli* | 655 |
| 25. | *E. coli* | 915 |
| 26. | *E. coli* | 26 |
| 27. | *E. coli* | 90 |
| 28. | *Escherichia blattae* | 846 |
| 29. | *Escherichia fregusonii* | 847 |
| 30. | *Escherichia hermani* | 848 |
| 31. | *Escherichia vulneris* | 850 |

Amplification Protocol

Amplification reactions were carried out on genomic DNA isolated from this test panel of microorganisms in the presence of individual primers from the group CN01-08. An example of the amplification protocol is shown below:

1. Add to a 0.6 ml microtube: 1.25 ul - genomic DNA at 20 ng/ul;
2. Prepare the following mixture: (Prepare fresh primer solutions from primer stocks).

| | |
|---|---|
| 10X reaction buffer | 5 ul |
| primer (10 μm) | 2.5 ul |
| dNTP mix (dATP, dCTP, dGTP and dTTP at 5 mM) | 2 ul |
| deionized water | 35 ul |

3. Add 44.5 ul of mix to each tube.
4. Heat reactions to 94° C. for 5 minutes and microfuge briefly.
5. Mix 1 part Taq polymerase with 3 parts Taq dilution buffer (10 mM Tris.HCl at pH 8.0, 1.0% Tween 20) and add 1.6 ul of diluted Taq polymerase to each tube, vortex and microfuge briefly. Taq polymerase may be readily acquired commercially, from Perkin Elmer Cetus, Norwalk, CT, for example.
6. Run 28 cycles of the temperature profile; 30 sec. at 93°; 5 min at 46°; 3 min ramp and 2 min at 72°. Automated thermal cyclers are readily available commercially, from Perkin Elmer Cetus, Norwalk, Conn., for example.
7. Take a 5.0 ul aliquot and run on acrylamide gel. The loading pattern should be: Time marker (TM), sample, sample, TM, sample, sample, etc. The final lane should contain time marker also.

Product Analysis

The amplification products were separated on a polyacrylamide gel. The formulation of the gel was 4% acrylamide/bisacrylamide at a ratio of 29/1. The electrophoresis running buffer was 0.5X TBE and the gels were run for 45 minutes at a field strength of 14V/cm. The resulting RAPD patterns were analyzed to determine which primers generated amplification products which were common to all the *Salmonella* serotypes but absent in the related genera. Such products were then be considered to be diagnostic for the presence of Salmonella DNA.

Several of the primers met the above criteria. As an example, amplification of the Salmonella and non-Salmonella test panels with the CN03 primer is shown in FIGS. 13 and 14. Lanes in the figures correspond to the sample numbering in Table 1. Time markers are at 228, 412, 693, 1331, and 2306 bp. An 800 base pair fragment appears to be conserved among the Salmonella, but not present in the non-Salmonella. In certain Salmonella, the 800 bp fragment is faint and difficult to see in Figures. The faintness of the desired bands probably results from competition for the 12-mer primer by other DNA sequences that generate amplified fragments. In addition, *Salmonella arizonae* bands are slightly shifted, even though the RAPD pattern looks similar. Despite these complications with the 12-mer primers, 17 to 23 mer primers chosen from sequences within the the amplified CN03 fragment produced bright bands and were conserved in greater than 99% of several hundred Salmonella strains tested.

Characterization of the Salmonella-Specific CN03 Amplification Product

To carry out a nested amplification based on the DNA sequence from a particular fragment it is necessary to first determine the exact sequence composition of the fragment. Although sequence determination may be done by any of several methods known in this art, in this instance the fragment, which was originally amplified from genomic DNA of *Salmonella typhimurium* Du Pont strain no. 587, was isolated from low-melting agarose and then reamplified in copious amounts. The reamplification product was then digested with a restriction enzyme to generate sequenceable fragments which did not have identical 12-base ends. The restriction products were resolved on a low-melting agarose gel and isolated. The initial sequences of these fragments was determined by the Sanger sequencing method using fluorescence-labeled dideoxynucleotides and the Genesis ™ 2000 DNA Analysis System. The primer CN03 was also used as the initial sequencing primer for both fragments. Once sequences that were internal to the CN03 primer were determined, portions of the CN03 Salmonella fragment were reamplified using these internal sequences. These same internal primers also then served as the sequencing primers.

From the sequenced CN03 fragment numerous primer pairs 17 to 26 bases in length were chosen for nested amplification. These primers, some of which are listed in Table 2, have greater than a 1000-fold selectivity for the amplification Salmonella genomic DNA sequences over the amplification of genomic DNA from related genera such as Citrobacter, Shigella, and Escherichia.

TABLE 2

Amplification Primers

Salmonella Primers:

| | | |
|---|---|---|
| 33-23-1.5 | 5' (GAC GCT AAA TGC GGT TAA CGC CA) 3' | SEQ ID NO.:9 |
| 33-23-5.8 | 5' (TCA GGA TGC AGG CGA TAG TAG CC) 3' | SEQ ID NO.:10 |
| 33-23-3 | 5' (AAC CAT GCA TCA TCG GCA GAA CG) 3' | SEQ ID NO.:11 |
| 33-23-6 | 5' (AGG CGA TAG TAG CCT GCC GCT TA) 3' | SEQ ID NO.:12 |
| 33-17-3 | 5' (AAC CAT GCA TCA TCG GC) 3' | SEQ ID NO.:13 |
| 33-17-6 | 5' (TAG TAG CCT GCC GCT | SEQ ID NO.:14 |

TABLE 2-continued

Amplification Primers

| | TA) 3' | |
|---|---|---|
| 33-17-1.5 | 5' (GGA CGC TTA ATG CGG TT) 3' | SEQ ID NO.:15 |
| 33-17-5.8 | 5' (ATT CAG GAT GCA GGC GA) 3' | SEQ ID NO.:16 |
| 33-17-9 | 5' (GGC TAA TCC AAG GGC AA) 3' | SEQ ID NO.:17 |
| 33-17-12A | 5' (TAT GAC CGT CCT CTC CT) 3' | SEQ ID NO.:18 |
| *E. coli* Primers: | | |
| 15-A2 | 5' (TAG CGG TGA AAT GCG) 3' | SEQ ID NO.:19 |
| 15-L | 5' (CAA GGC ATC CAC CGT) 3' | SEQ ID NO.:20 |
| 15-G | 5' (GAA GTC GTA ACA AGG) 3' | SEQ ID NO.:21 |
| 15-Y | 5' (TCC TGG GCC TCT AGA) 3' | SEQ ID NO.:22 |

Selection of *E. coli* Target Segment

If a segment of nucleic acid which is characteristic to a particular organism is already known, the instant invention provides a convenient means to amplify that segment in order to identify the presence of the particular organism. In the instant case for example, a specific unique segment of the *E. coli* genome was known to Applicants and was used to practice Applicants' improved nested PCR process to detect the presence of *E. coli*. Primer sequences from within the ribosomal RNA operon of *E. coli* were chosen to demonstrate the nesting. The operon sequence was published by Brosius, J. et al. in J. Mol. Biol., 148, 107, 1981.

Nested PCR Methods

A. Amplification Protocols

All amplifications were carried out in Perkin Elmer 9600 Thermocycler under the following conditions:

| | |
|---|---|
| Denaturation: | 94° C., 15 seconds |
| Annealing: | Time and temperature indicated in examples |
| Extension: | 72° C., 60 seconds. |
| No. of Cycles: | Indicated in examples |
| Amplification Reagents: | |
| Buffer: | 50 mM KCl, 10 mM Tris-HCl, pH8.3, 1.5 mM MgCl$_2$, 0.001% gelatin |
| dNTP's: | 200 μM |
| Tween 20: | 0.57% |
| Primers: | Indicated in examples |
| Enzyme: | Native Taq polymerase from Perkin Elmer, 0.05 units/μl |
| Total and DNA Sample Volume: | Indicated in examples |

B. Gel Electrophoresis

Amplified samples were electrophoresed on 4% polyacrylamide gels, ethidium bromide stained, and observed on a transilluminator. Photographs of gels were captured on a Photometrics Limited Star 1 CCD camera interfaced to a computer and the images digitally stored for later processing. The images were inverted so that bands appear dark in a light background. The marker band sizes are 228, 412, 693, 1331, and 2306 bp.

C. Preparation of Salmonella DNA Samples

*Salmonella typhimurium* Du Pont strain no.1084 was grown in BHI broth at 37° C. for 16 hours to a final culture population of approximately $5\times10^8$ colony forming units per milliliter. Serial 10-fold dilutions of the culture were made in 0.1% peptone water to give suspensions of 1/10th, 1/100th, 1/1000th, 1/10,000th, and 1/100,000th of the original population. DNA extracts were made from all of these suspensions according to the following protocol: 500 μl of bacterial suspension, 500 μl of 2 mg/ml proteinase K in 50 mM tris pH 8, and 50 μl of 1% sodium dodecyl sulfate were mixed and incubated first at 55° C. for 30 minutes and then at 94° C. for 10 minutes. The samples were aliquoted and frozen at −20° C. The 6 sequential 10-fold decreasing concentrations of Salmonella DNA and the peptone water blank are designated Salmonella samples 1–7.

D. Preparation of *E. coli* DNA Samples

*E. coli* Du Pont strain no. 925, was grown in BHI broth at 37° C. for 16 hours to a population density of approximately $2\times10^9$ colony forming units per milliliter. This culture was serially 10-fold diluted in peptone water and the DNA extracted in the identical manner as the Salmonella. The 6 sequentially decreasing concentrations of *E. coli* DNA and the peptone water blank are designated *E. coli* samples 1–7.

E. Estimation of Amplification Factors

Figure 1B:
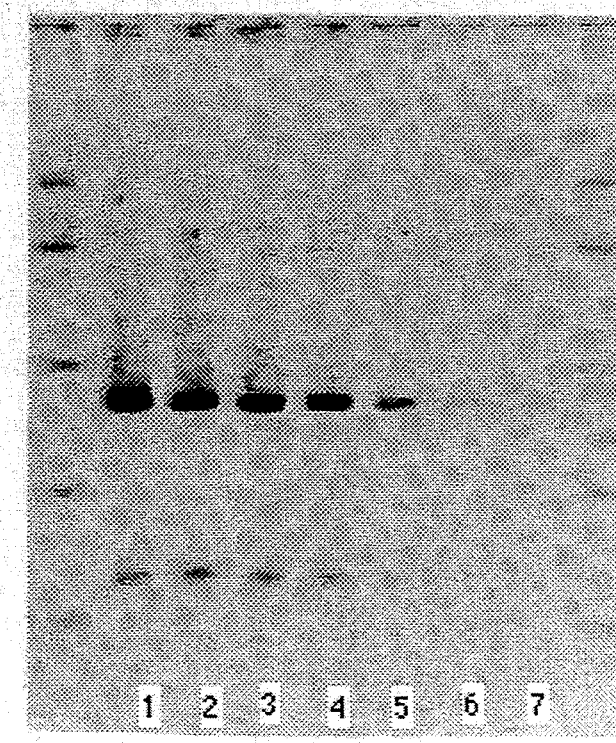

It is necessary to estimate amplification factors to evaluate the kinetic parameters of the model. An approximate method to obtain amplification factors is presented here. Salmonella DNA samples 1–7 were amplified using primers 33-17-3 and 33-17-6 (Table 2) at 0.48 μM each, an annealing time of 2 minutes, and an annealing temperature of 61° C. 5 μl of the sample was used in a total reaction volume of 50 μl FIG. 1 shows the results of the amplification carried out for 10 and 28 cycles. From these gels, it was possible to estimate the amplification factor necessary to generate a faintly visible band from any of the serial dilutions of Salmonella DNA. With 10 cycles of amplification, a faint band is visible in lane 1 (Salmonella sample 1), and no bands at higher dilutions. With 28 cycles of amplification, a faint band is visible in sample 6, and bright bands at higher starting DNA concentrations. It is assumed that the amplified DNA concentration in lane 1 of the 10 cycle gel and lane 6 of the 28 cycle gel are approximately equal. Invoking equation 6 of the kinetic model, and recognizing that the samples are serial 10-fold dilutions, the following equation can be written:

$$(1+E)^{10}\times 10^5=(1+E)^{28} \qquad (15)$$

Solving equation (15), E=0.9, meaning that in an average cycle, 90% of the DNA is replicated. The amplification factor necessary to generate a faint band from sample 1 is $(1+E)^{10}$, or about 600. The amplification factor necessary to generate a faint band from any of the samples 1–6 is $600\times 10^{(n-1)}$, where n is the sample number.

Figure 2A:
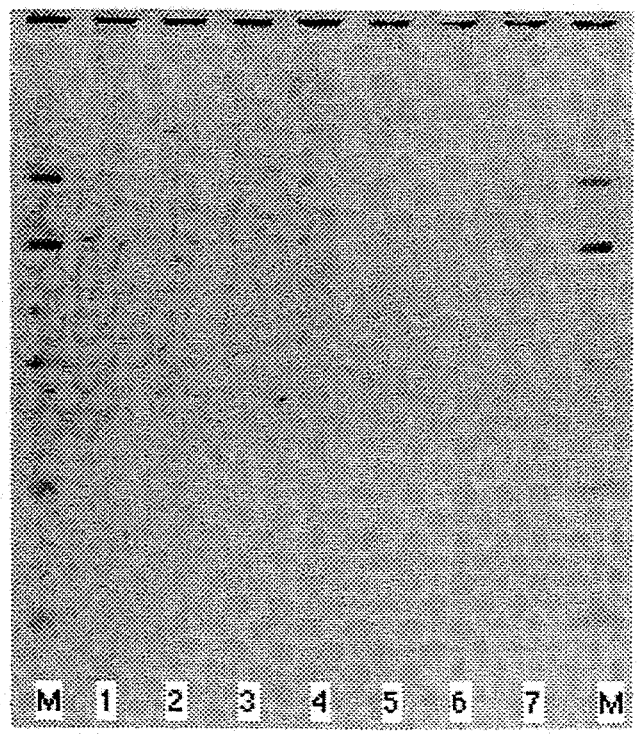
FIG. 2 compares 8 (FIG. 2A) and 27 (FIG. 2B) cycle PCR amplifications of *E. coli* DNA, using primers 15-A2 and 15-L (Table 2). Samples 1-6 are serial 10-fold dilutions of the DNA, the highest concentration sample being $2 \times 10^9$ copies of genomic DNA per milliliter, based on viable cell counts. Sample 7 is a control with no *E. coli* DNA.
Figure 2B:
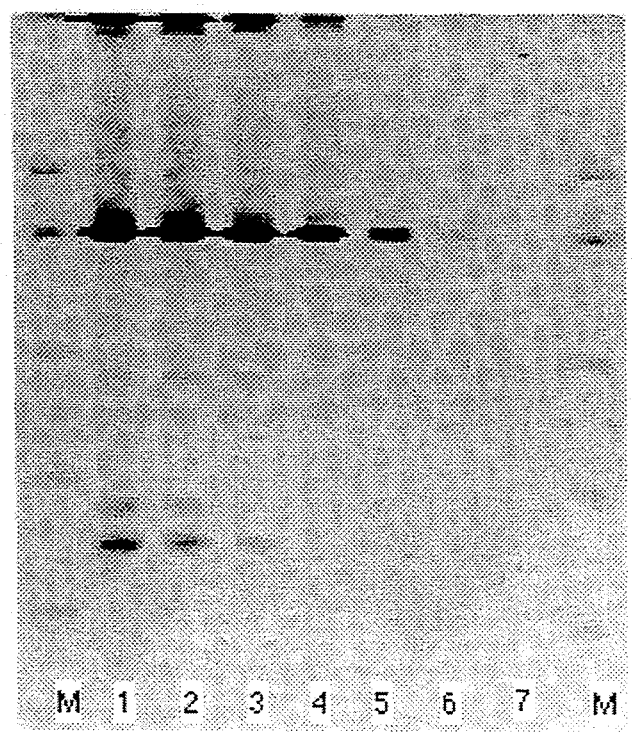
Figure 3A:
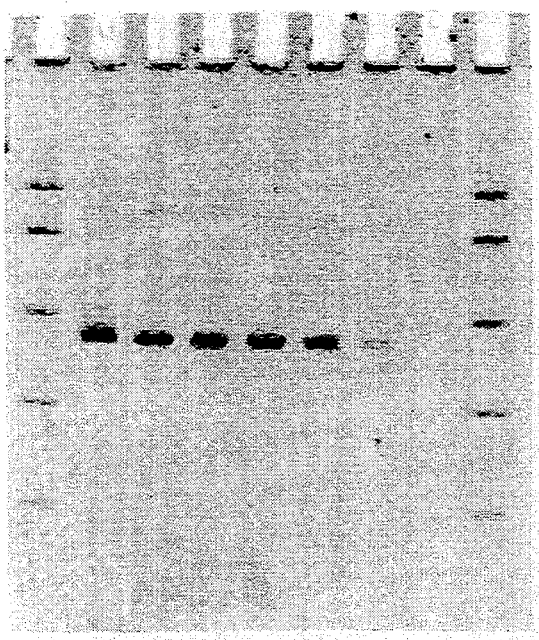
Figure 3B:
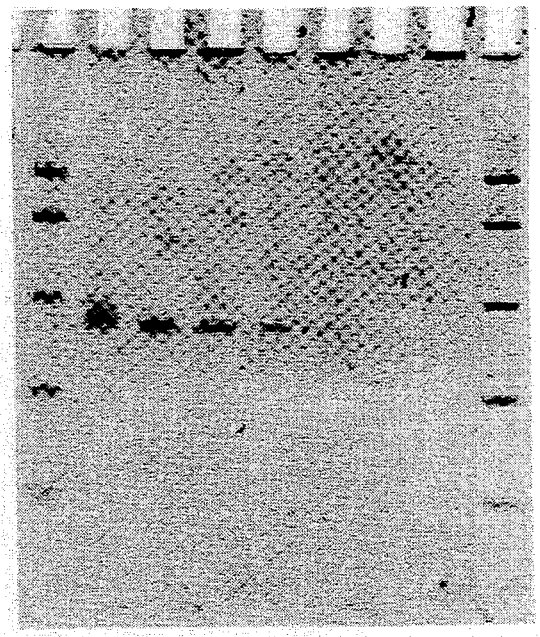
Figure 3C:
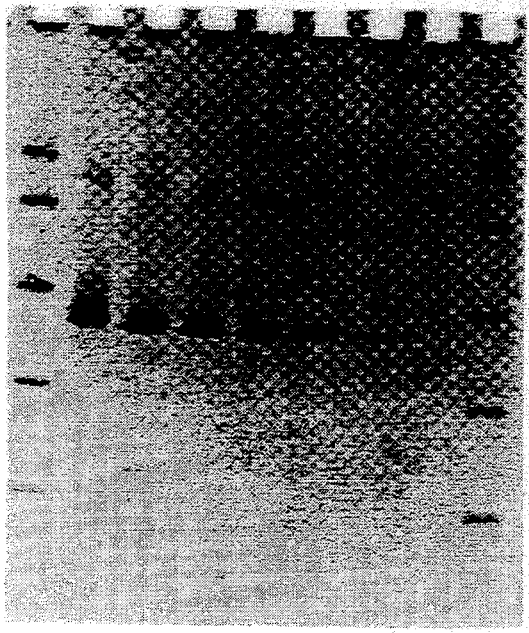
Figure 3D:
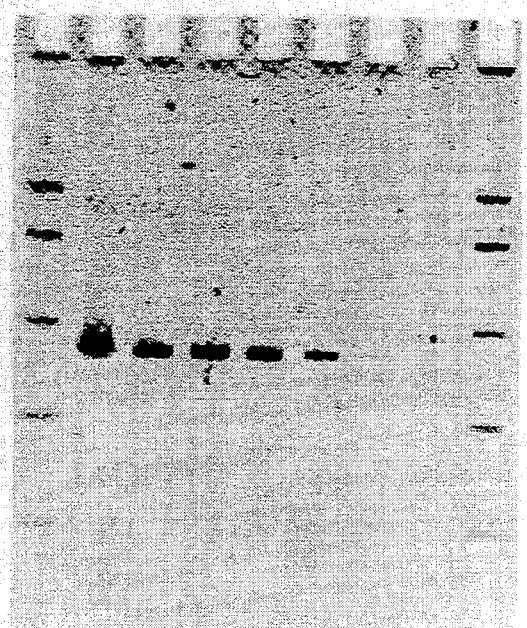
Figure 3E:
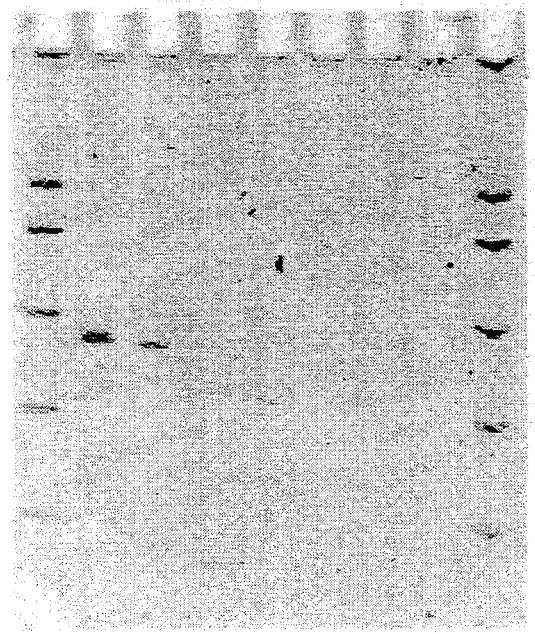
Figure 3F:
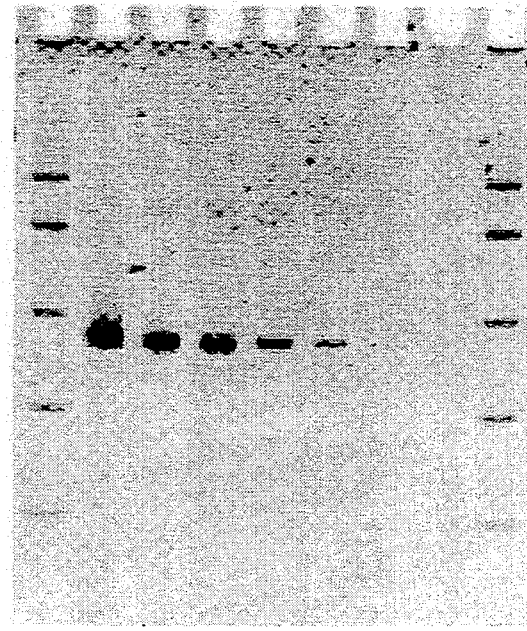
Figure 3G:
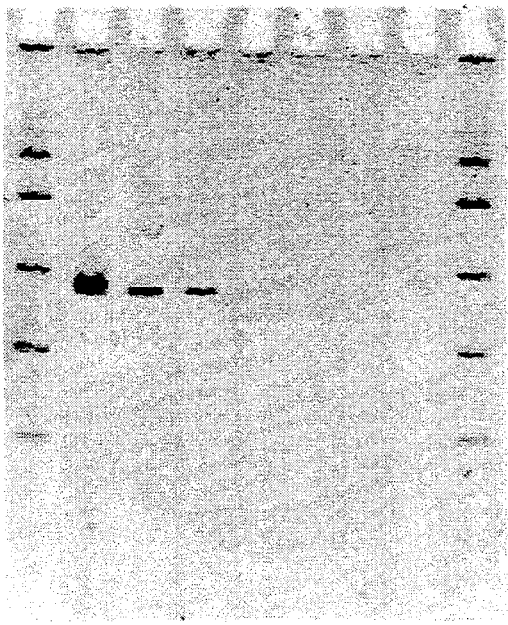
Figure 3H:
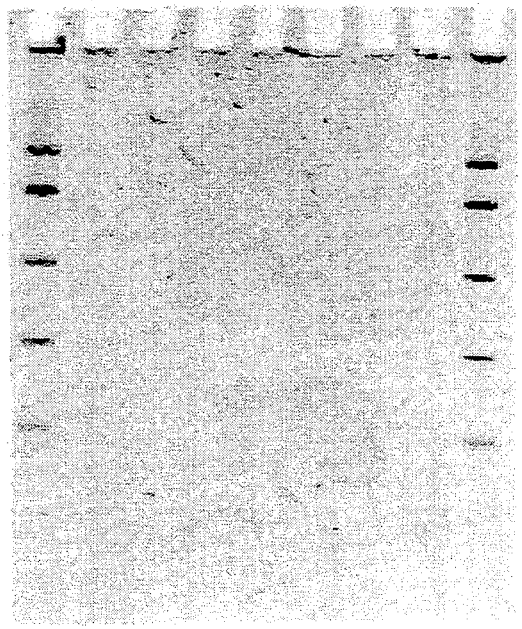

The *E. coli* DNA samples were amplified using primers 15-A2 and 15-L (Table 2) at 0.53 μM each, with annealing at 55° C. for 2 minutes. 1 μl of the DNA sample was used in a 25 μl total reaction volume. The result of the amplification for 8 cycles and 27 cycles is shown in FIG. 2. With 8 cycles, sample 1 produces a faint band, while more dilute sample lanes are blank. With 27 cycles, sample 6 produces a faint band while the more concentrated samples yield bright bands. Using the same arguments as in the case of the Salmonella DNA:

$$(1+E)^8 \times 10^5 = (1+E)^{27} \quad (16)$$

Solving equation 16, E=0.83, and the amplification factor necessary to generate a faint band from *E. coli* DNA sample 1 is approximately 120. The amplification factor to produce bands from the other sample dilutions is $120 \times 10^{(n-1)}$ where n is the *E. coli* sample number.

F. Estimation of Primer Annealing Kinetic Parameters

Amplification factors were estimated by the methods of section E at a number of different primer concentrations and annealing times. Equation 6 was fit to this data in order to evaluate the parameters $\epsilon_{max}$ and k.

Salmonella samples 1–7 were amplified using primers 33-17-3 and 33-17-6 at the concentrations and annealing times shown in FIG. 3. 5 μl of the DNA sample was used in a total volume of 50 μl. The amplification was carried out for 32 cycles at an annealing temperature of 61° C. For each combination of primer concentration p and annealing time t, a sample number "n" could be chosen such that sample n had a faint band. Unless n was 1 or 6, higher number samples had no band and lower numbered samples had bright bands. For example, with a primer concentration 0.0167 μM and an annealing time of 1.6 minutes, sample 4 met the above criteria. The amplification factor could then be estimated by the method above to be $600 \times 10^{(n-1)}$. In some cases, a faint band was visible in the original gel, but not visible in the reproduction of FIG. 3. It is recognized that the designated faint bands used to estimate the amplification factors can vary in the DNA copy number. However, these methods have proven to be sufficiently accurate to allow for the efficient practice of this invention.

TABLE 3

Data from Amplification of Salmonella DNA with Primers 33-17-3 and 33-17-6

| P, uM | t, min | n | A | pt | E |
|---|---|---|---|---|---|
| 0.0167 | 10 | >6 | | 0.167 | |
| 0.0048 | 10 | 5 | 6.00E + 06 | 0.048 | 0.63 |
| 0.038 | 5.15 | >6 | | 0.196 | |
| 0.0167 | 5.15 | 6 | 6.00E + 07 | 0.086 | 0.75 |
| 0.0048 | 5.15 | 3 | 6.00E + 04 | 0.025 | 0.41 |
| 0.038 | 1.6 | 6 | 6.00E + 07 | 0.061 | 0.75 |
| 0.0167 | 1.6 | 4 | 6.00E + 05 | 0.027 | 0.52 |
| 0.0048 | 1.6 | <1 | | 0.008 | |
| 0.038 | 0.86 | 4 | 6.00E + 05 | 0.033 | 0.52 |
| 0.0167 | 0.86 | 2 | 6.00E + 03 | 0.014 | 0.31 |

P = Primer Concentration, μM
t = Annealing Time, min
n = Salmonella sequential sample number amplified to a faint band (< or >, none of samples showed faint band)
A = Amplification factor = $600 \times 10^{(n-1)}$
E = *Per cycle amplification efficiency* = $A^{(1/32)} - 1$, 32 = no. of cycles Table 3 summarizes the results of FIG. 3. For each primer concentration and annealing time, the sample number designated as the faint band, the amplification factor A calculated by the above methods, and the per cycle primer amplification efficiency, ($E = A^{1/N}$, N=cycle number) are shown. An "n" tabulated as >6 indicates that the most dilute sample produced a bright band. An "n" of <1 indicates that no band was seen in even the most concentrated sample. These points were not used in the estimation of kinetic parameters.

Figure 4:
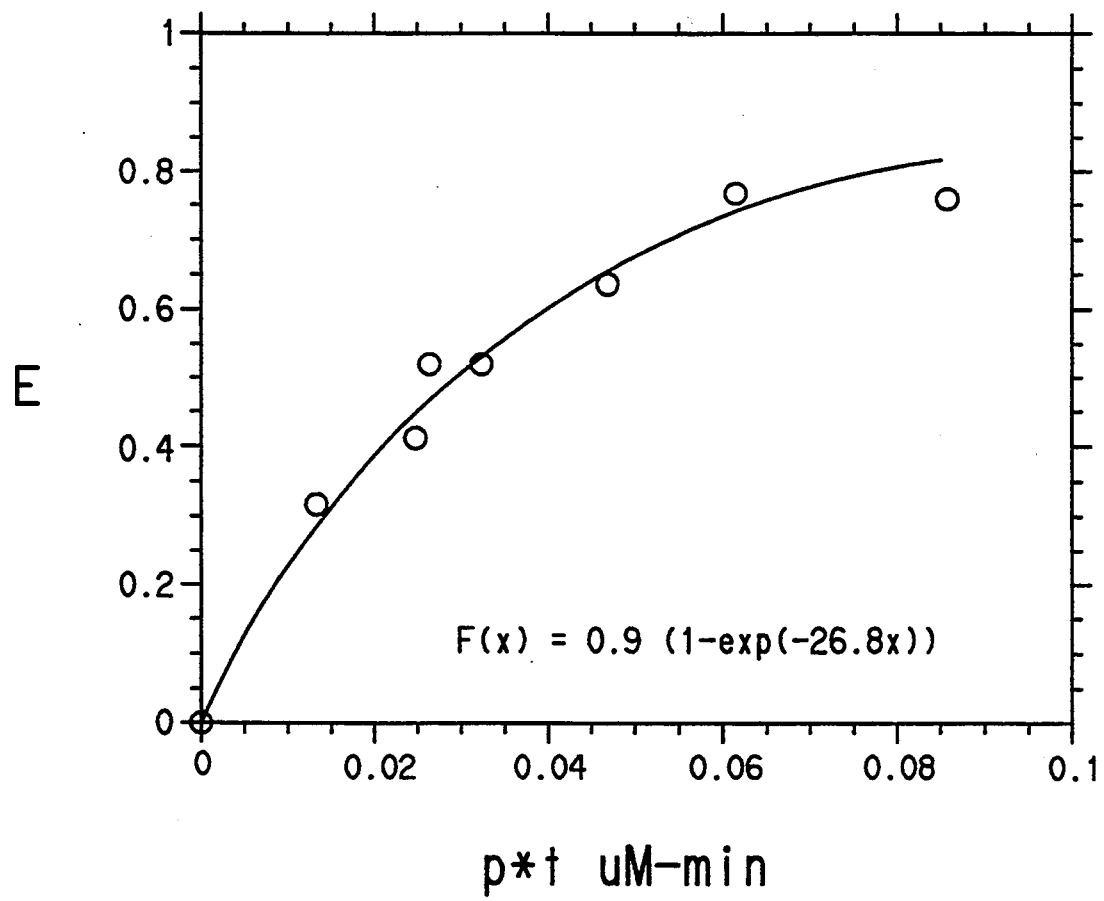
FIG. 4 is a plot of the per stage amplification efficiency versus the product of the primer concentration and annealing time obtained from the data of FIG. 3 and Table 3. The optimal fit of the kinetic model to the data is also shown.
Figure 5A:
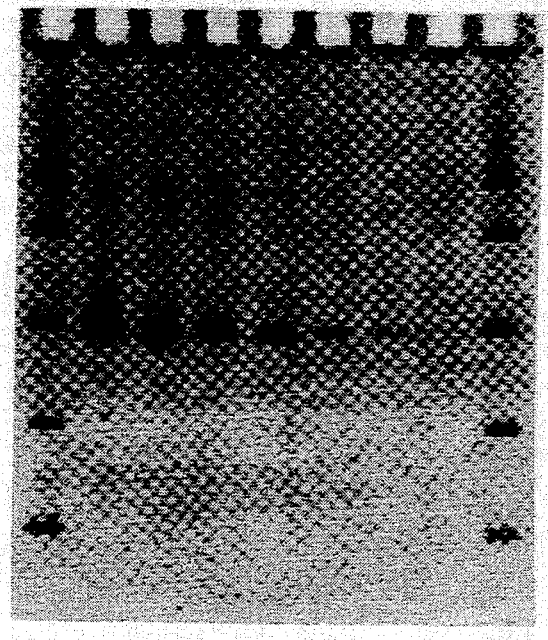
FIGS. 5A-5J compares the amplification of the *Salmonella typhimurium* DNA with primers 33-17-1.5 and 33-17-5.8 (Table 2) at various primer concentrations and annealing times. The same samples as in FIG. 1 were used.
Figure 5B:
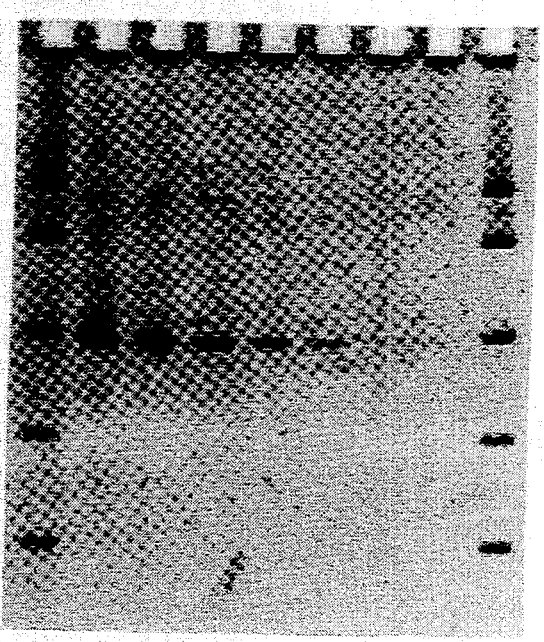
Figure 5C:
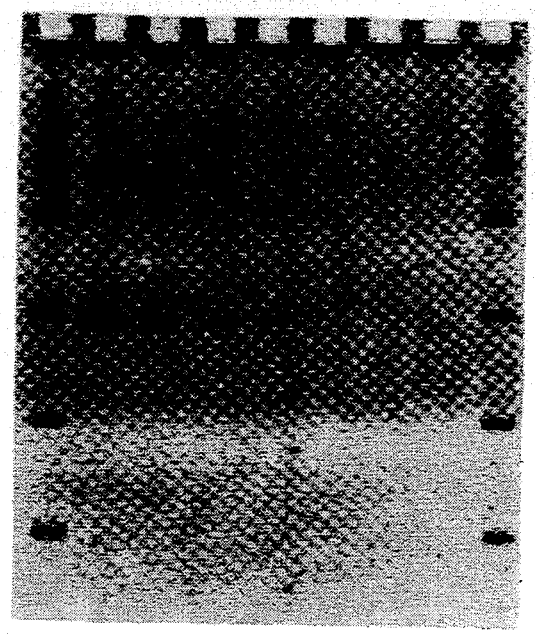
Figure 5D:
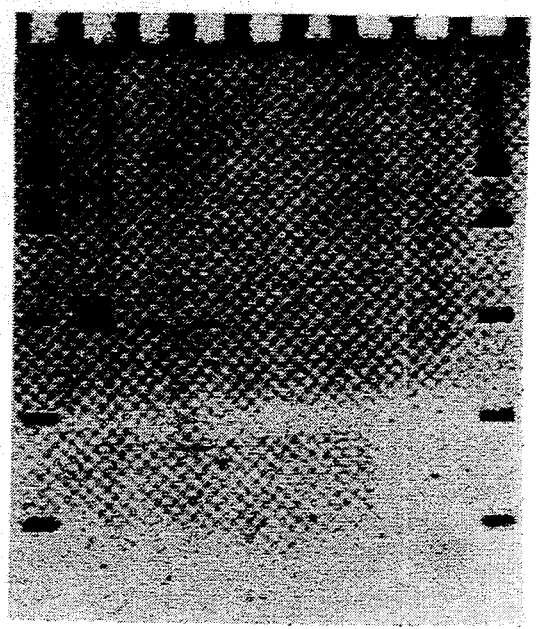
Figure 5E:
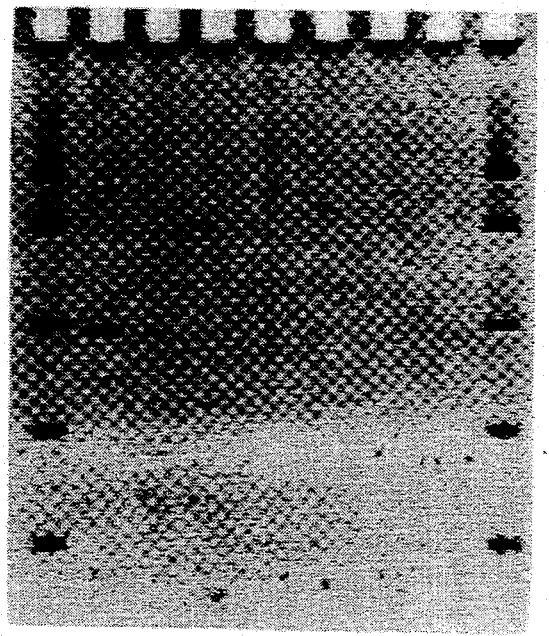
Figure 5F:
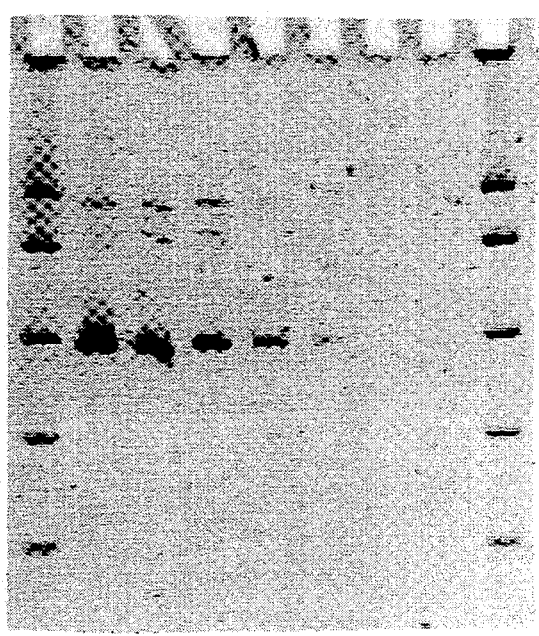
Figure 5G:
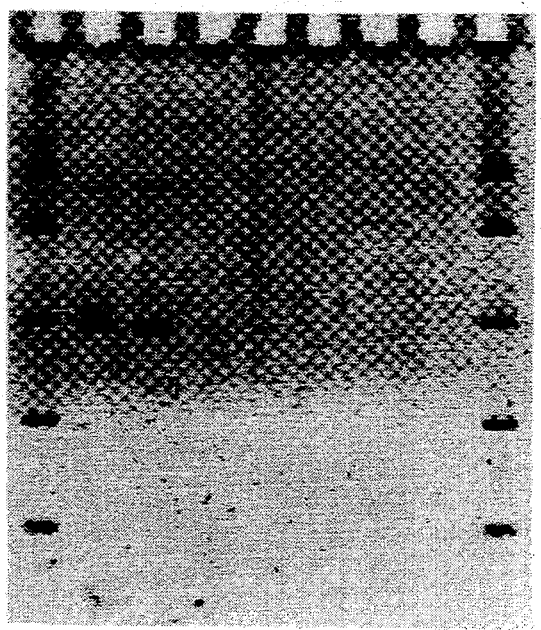
Figure 5H:
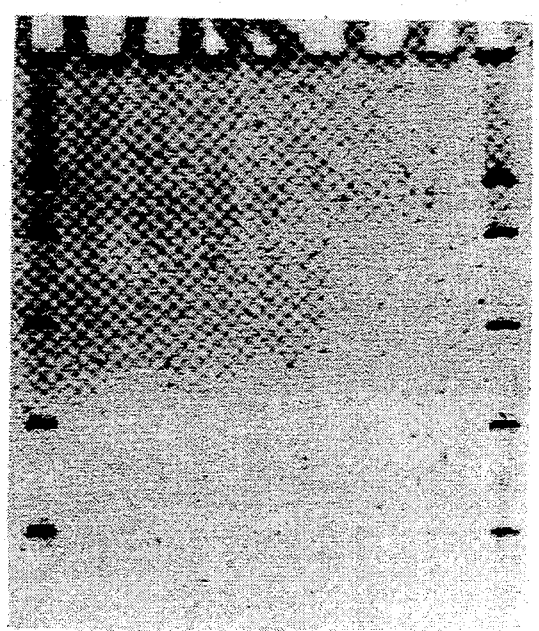
Figure 5I:
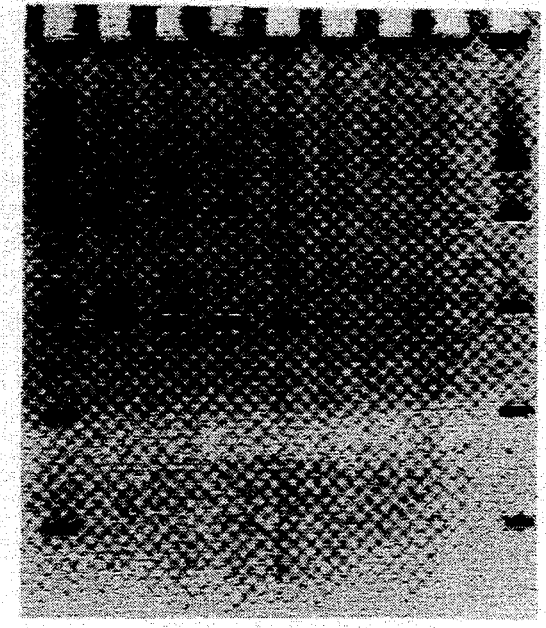
Figure 5J:
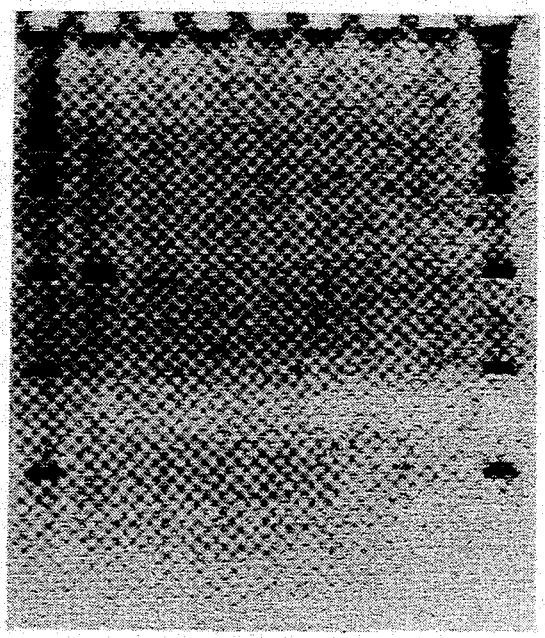

The per cycle efficiency E is plotted as a function of the product of the primer concentration and the annealing time (p*t) in FIG. 4. Equation 6 of the kinetic model was optimally fit to the data to give the equation: E=0.9 (1−exp(−26.8 pt)). The kinetic parameters for the annealing of primers 33-17-3 and 33-17-6 to Salmonella DNA are $\epsilon_{max}=0.9$ and k=26.8 (μM−min)$^{-1}$.

Figure 6:
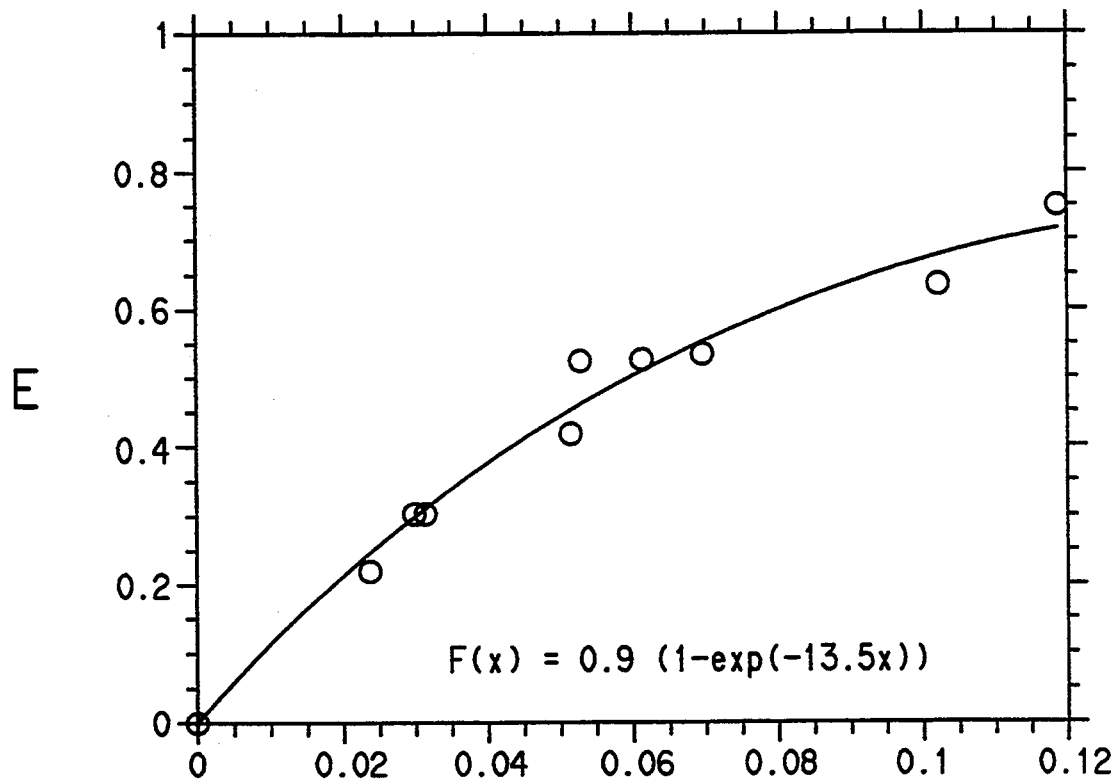
FIG. 6 is a plot of the per stage amplification efficiency versus the product of the primer concentration and annealing time obtained from the data of FIG. 5 and Table 4. The optimal fit of the kinetic model to the data is also shown.
Figure 7A:
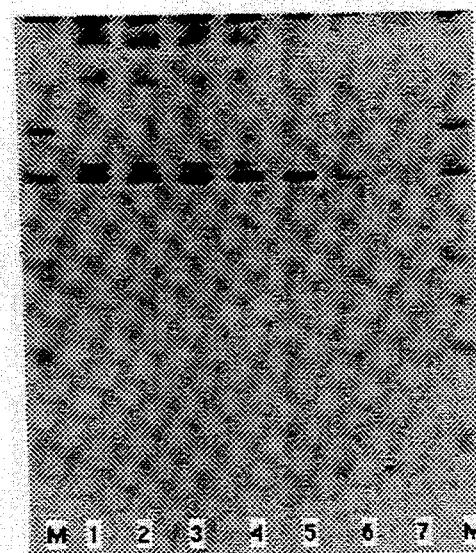
Figure 7B:
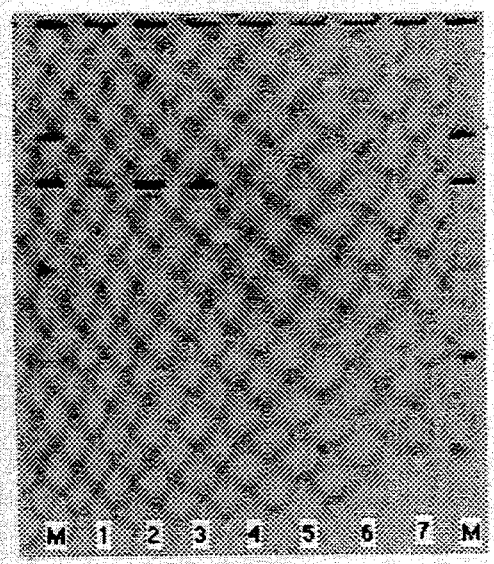
Figure 7C:
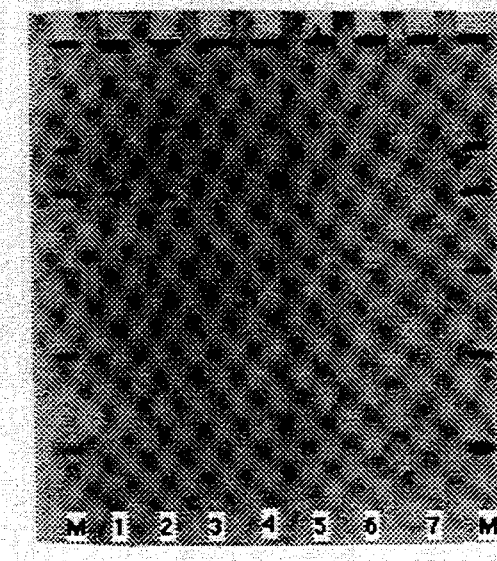
Figure 7D:
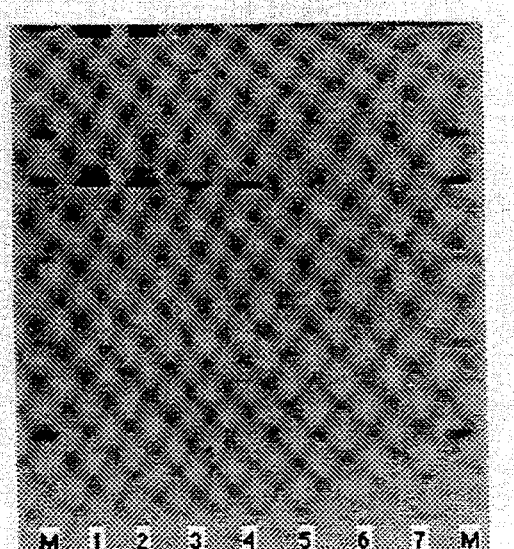
Figure 7E:
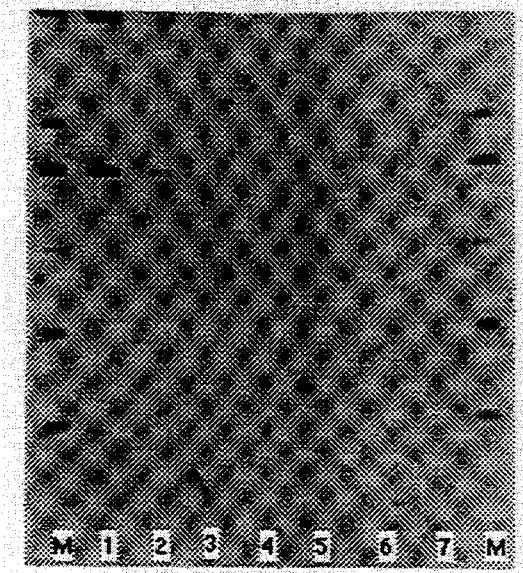
Figure 7F:
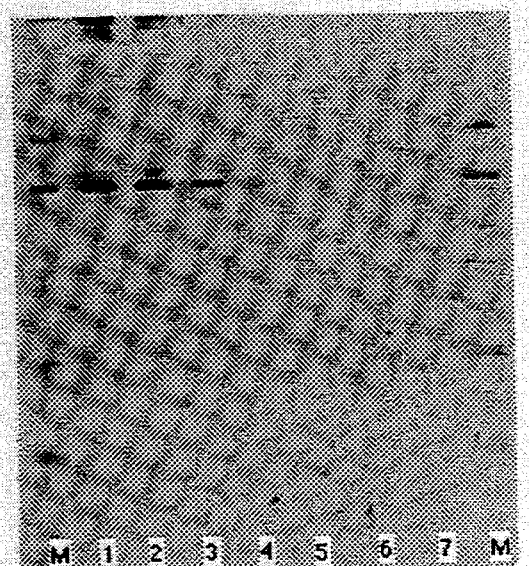
Figure 7G:
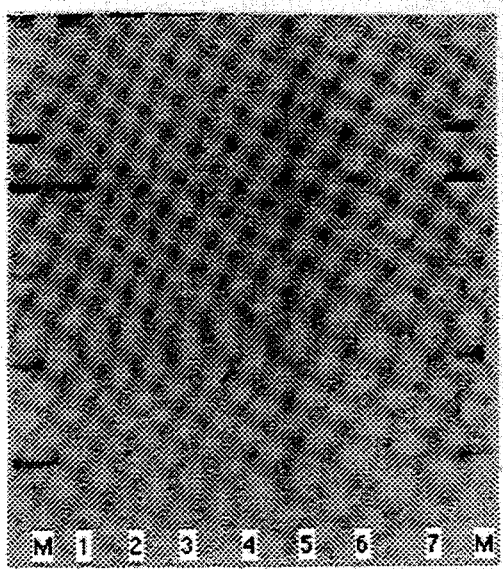
Figure 7H:
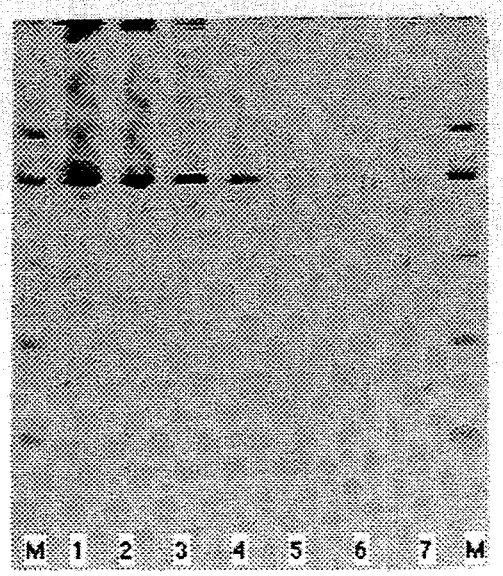

Salmonella samples 1–7 were amplified with primers 33-17-1.5 and 33-17-5.8 at the primer concentrations and annealing times shown in FIG. 5. All other amplification conditions were identical to those of primers 33-17-3 and 33-17-6. The sample numbers giving faint bands, the amplification factors and the per cycle efficiencies are shown in Table 4. The data is plotted and optimally fit with the kinetic model in FIG. 6. The kinetic parameters for 33-17-1.5 and 33-17-5.8 are $\epsilon_{max}=0.9$ and k=13.5 (μM−min)$^{-1}$.

TABLE 4

Data from Amplification of Salmonella DNA with Primers 33-17-1.5 and 33-17-5.8

| P, uM | t, min | n | A | pt | E |
|---|---|---|---|---|---|
| 0.034 | 7 | >6 | | 0.238 | |
| 0.017 | 7 | 6 | 6.00E + 07 | 0.119 | 0.75 |
| 0.0075 | 7 | 4 | 6.00E + 05 | 0.053 | 0.52 |
| 0.017 | 4.05 | 4 | 6.00E + 05 | 0.069 | 0.52 |
| 0.0075 | 4.05 | 2 | 6.00E + 03 | 0.030 | 0.31 |
| 0.034 | 3 | 5 | 6.00E + 06 | 0.102 | 0.63 |
| 0.017 | 3 | 3 | 6.00E + 04 | 0.051 | 0.41 |
| 0.0075 | 3 | 1 | 6.00E + 02 | 0.023 | 0.22 |
| 0.034 | 1.8 | 4 | 6.00E + 05 | 0.061 | 0.52 |
| 0.017 | 1.8 | 2 | 6.00E + 03 | 0.031 | 0.31 |

P = Primer Concentration, μM
t = Annealing Time, min
n = Salmonella sequential sample number amplified to a faint band (< or >, none of samples showed faint band)
A = Amplification factor = $600 \times 10^{(n-1)}$
E = *Per cycle amplification efficiency* = $A^{(1/32)} - 1$, 32 = no. of cycles

Figure 8:
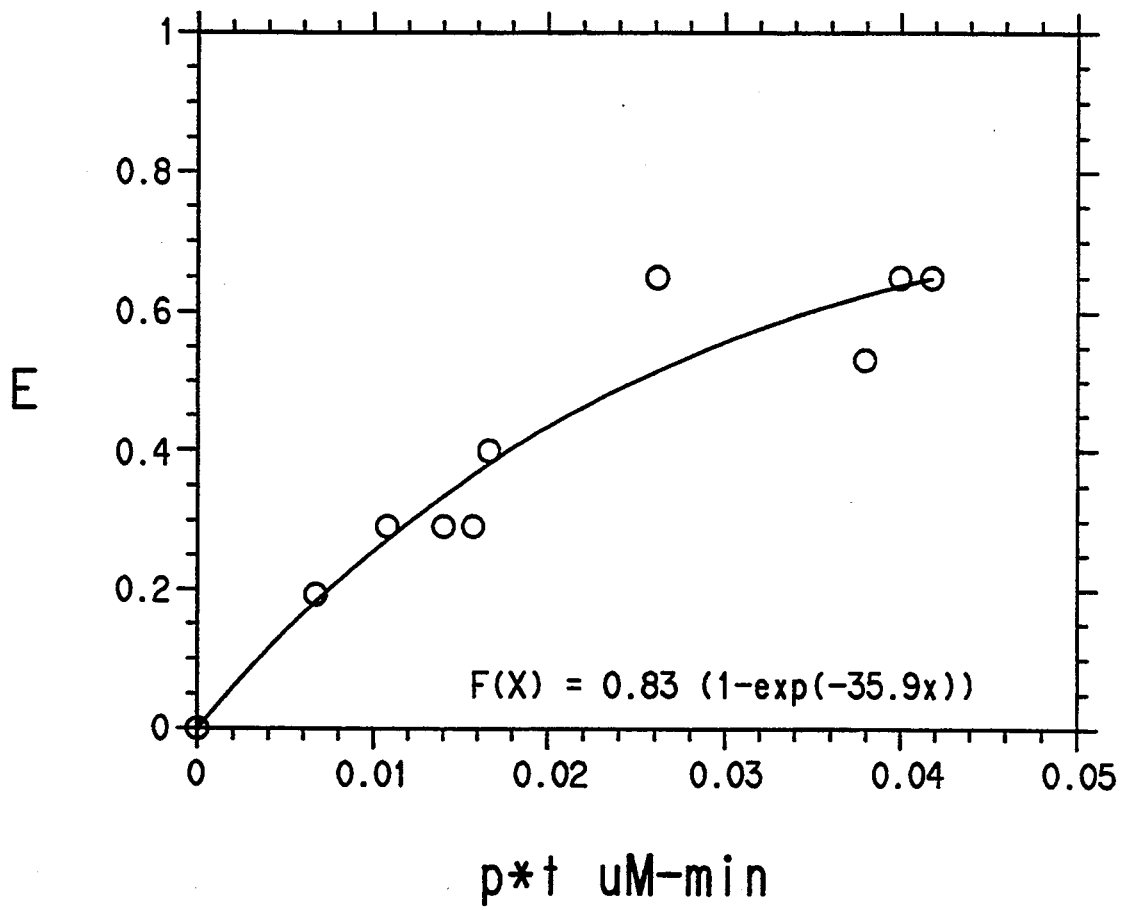
FIG. 8 is a plot of the per stage amplification efficiency versus the product of the primer concentration and annealing time obtained from the data of FIG. 7 and Table 5. The optimal fit of the kinetic model to the data is also shown.

*E. coli* samples 1–7 were amplified with primers 15-A2 and 15-L at the primer concentrations and annealing times shown in FIG. 7. 1 μl of the DNA sample in a total reaction volume of 25 μl was amplified for 28 cycles with a 55° C. annealing temperature. The data is summarized in Table 5 and plotted in FIG. 8. The kinetic parameters for these primers are $\epsilon_{max}=0.83$ and k=35.9 (μM−min)$^{-1}$.

TABLE 5

Data from Amplification of E. coli DNA with Primers 15-A2 and 15-L

| P, uM | t, min | n | A | pt | E |
|---|---|---|---|---|---|
| 0.016 | 6 | >6 | | 0.096 | |
| 0.0064 | 6 | 4 | 1.20E + 05 | 0.038 | 0.52 |
| 0.0024 | 6 | 2 | 1.20E + 03 | 0.014 | 0.29 |
| 0.016 | 2.5 | 5 | 1.20E + 06 | 0.040 | 0.65 |
| 0.0064 | 2.5 | 2 | 1.20E + 03 | 0.016 | 0.29 |
| 0.017 | 1.6 | 5 | 1.20E + 06 | 0.027 | 0.65 |
| 0.0069 | 1.6 | 2 | 1.20E + 03 | 0.011 | 0.29 |
| 0.042 | 1 | 5 | 1.20E + 06 | 0.042 | 0.65 |
| 0.017 | 1 | 3 | 1.20E + 04 | 0.017 | 0.40 |
| 0.0069 | 1 | 1 | 1.20E + 02 | 0.007 | 0.19 |

P = Primer Concentration, μM
t = Annealing Time, min
n = E. coli sequential sample number amplified to a faint band (< or >, none of samples showed faint band)
A = Amplification factor = $120 \times 10^{(n-1)}$
E = *Per cycle amplification efficiency* = $A^{(1/28)} - 1$, 28 = no. of cycles

EXAMPLES

EXAMPLE 1

Primers 33-17-9 and 33-17-12a (Table 2) amplify a sequence nested within the amplification product of primers 33-17-3 and 33-17-6 within the Salmonella genome. In this example, these two primer pairs were nested according to the method of the invention. The procedure was designed using the inequality constraints of equations 9-18 and with the annealing kinetic parameters experimentally evaluated for each primer set. The cycling conditions were:

First stage outer primer concentration, $P_{011} = 0.0076$ μM

Second stage inner primer concentration, $P_{022} = 0.48$ μM

First stage annealing time, $t_1 = 8$ minutes
Second stage annealing time, $t_2 = 0.8$ minutes
First stage reaction volume, $V_1 = 25$ μl
Second stage reaction volume, $V_2 = 50$ μl
Number of cycles in first stage, $N_1 = 20$
Number of cycles in second stage, $N_2 = 20$ The kinetic parameters for primers 33-17-3 and 33-17-6 (from data of section F) and for 33-17-9 and 33-17-12a (data not shown) are:

$k_1 = 26.8 \, (\mu M - \min)^{-1}$ $k_2 = 18.5 \, (\mu M - \min)^{-1}$ $\epsilon_{max\,1} = 0.9$ $\epsilon_{max\,2} = 0.75$ Under these conditions, inequality constraints 9-15 are satisfied as follows:

| | (requirement) |
|---|---|
| $\epsilon_{max\,1}(1-\exp-(k_1 P_{011} t_1)) = .72$ | $> 0.4$ |
| $\epsilon_{max\,2}(1-\exp-(k_2 P_{022} t_2)) = .75$ | $> 0.4$ |
| $\epsilon_{max\,1}(1-\exp-(k_1 P_{012} t_2)) = 0.07$ | $< (1/5)\epsilon_{max\,2}*$ $(1-\exp-(k_2 P_{022} t_2))$ |
| $k_1 P_{011} t_1 = 1.63$ | $1.2 < k_1 P_{011} t_1 < 2.3$ |
| $k_2 P_{022} t_2 = 7.1$ | $1.2 < k_2 P_{022} t_2$ |
| $V_2 t_1 / V_1 t_2 = 20$ | $15 < V_2 t_1 / V_1 t_2$ |
| $V_2 / V_1 = 2$ | $2 < V_2/V_1 < 4$ |

In addition, the parameters are well within the boundaries of conditions 16 and 17 for $V_2/V_1=2$.

Figure 9A:
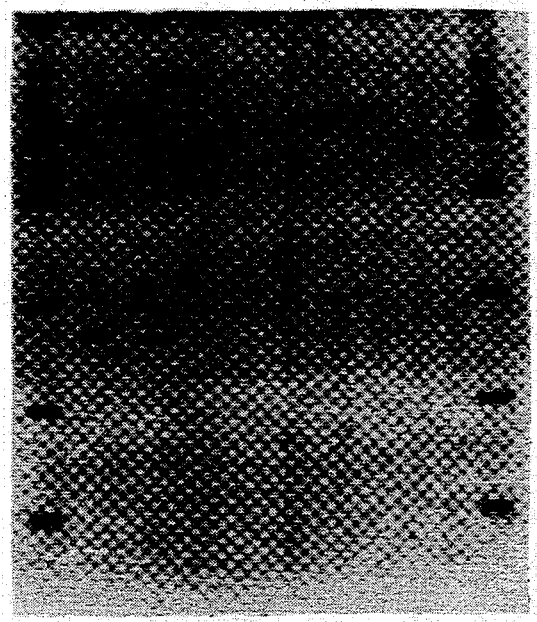
FIGS. 9A-9E demonstrates the kinetically controlled nesting with outer primers 33-17-3 and 33-17-6 and inner primers 33-17-9 and 33-17-12a using the Salmonella DNA samples described in FIG. 1. Shown are the results of each stage separately, the two stages combined, and the first stage done twice in sequence.

In FIG. 9A, Salmonella samples 1-7 were carried through the 20 cycles of only the first stage of nesting. The annealing temperature was 61° C. and the reaction mixture contained 1 μl of the genomic DNA sample. At the end of this process, a band was visible in Salmonella dilution 2, but in none of the more dilute samples. Using the methods of section E, the amplification factor of the outer primers in the first stage can be estimated at 15,000, and the per stage efficiency at 0.61. This exceeds the minimum per stage efficiency of 0.4 required in the definition of the invention. In addition, this measured efficiency is close to the 0.72 efficiency predicted by the kinetic model $E_{11} = \epsilon_{max\,1}(1-\exp-(k_1 P_{011} t_1))$.

Figure 9B:
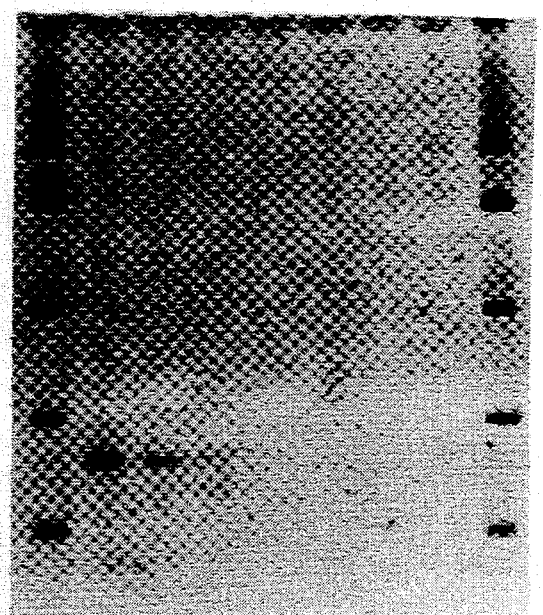

In FIG. 9B, the samples were amplified in the second stage only. This was accomplished by performing the first stage in the identical manner as in FIG. 9A, only the Taq polymerase was omitted. Prior to the second stage, the 25 μl of additional buffer mix containing 0.96 μM of the nested (33-17-9 and 33-17-12A) primers and Taq polymerase was added to the product of the first stage of amplification. Amplification then continued for the 20 additional cycles with the reduced annealing time. A faint 33-17-9 and 33-17-12A primed band was visible in Salmonella sample 3. This corresponds to a 150,000-fold amplification by the inner primers in the second stage, giving a per stage efficiency of 0.81. This exceeds the minimum required efficiency of 0.4. Again, the measured efficiency was close to the 0.75 value predicted by the model $E_{22} = \epsilon_{max\,1}(1-\exp-(k_2 P_{022} t_2))$.

Figure 9C:
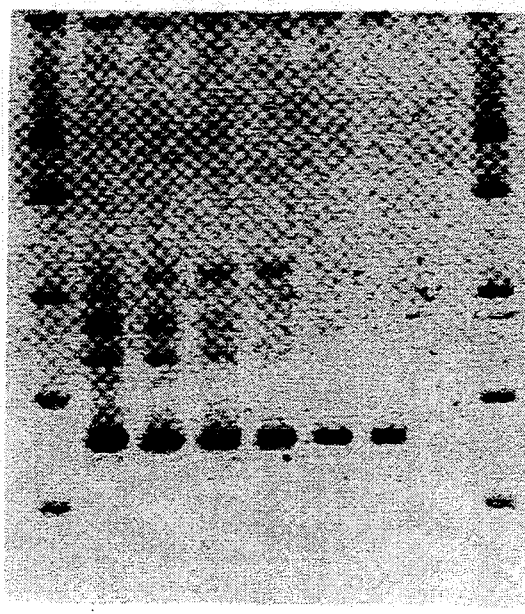

In FIG. 9C, both stages of amplification were active. The same protocol was followed as described for FIG. 9B, only the Taq polymerase was present in the first stage. The product of the inner primers is brightly visible in even the most dilute Salmonella sample 6. The overall amplification factor of both stages was greater than $10^8$. Therefore, nesting must have been accomplished, since the amplification factor of both stages together is much greater than each of the stages individually. In addition, the nesting meets the requirement that the entire product of the first stage be used in the second stage, and that the second stage primers be added prior to the second stage.

Figure 9D:
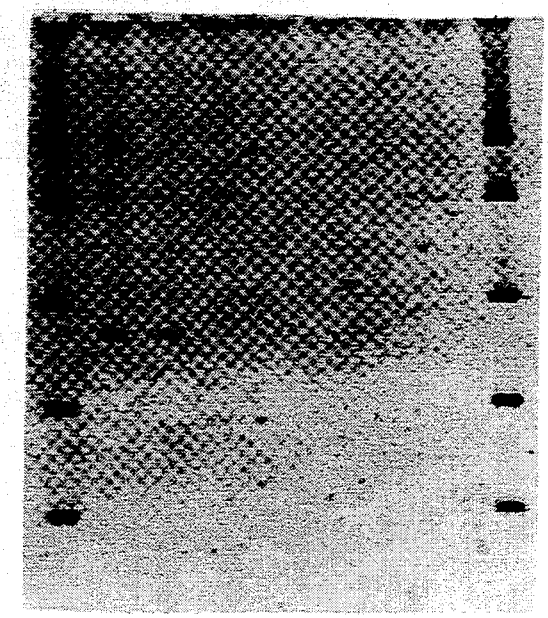

In FIG. 9D, the identical protocol was followed as in 9C, only the nested primers (33-17-9 and 33-17-12a) were omitted from the mix added prior to the second stage. With this procedure, a faint 33-17-3, 33-17-6 primer product was seen in sample 2, which was also the highest sample number that generated a band after the first stage only. Since the samples are serial 10-fold dilutions, the amplification factor of the first primer set in the second stage must have been less than 10, giving a per cycle efficiency of less than 0.12. This efficiency satisfies the criterion of the invention that in each cycle of the second stage, at least 5 times as much extension product is made from the nested primers than from the outer primers. In this case, the efficiency ratio was greater than 0.81/0.12, which is greater than 5. Again, the kinetic model accurately predicted the the efficiency of the outer primers in the second stage as $E_{12} = \epsilon_{max\,1}(1-\exp-(k_1 P_{012} t_2)) = 0.07$, which is less than 0.12.

Figure 9E:
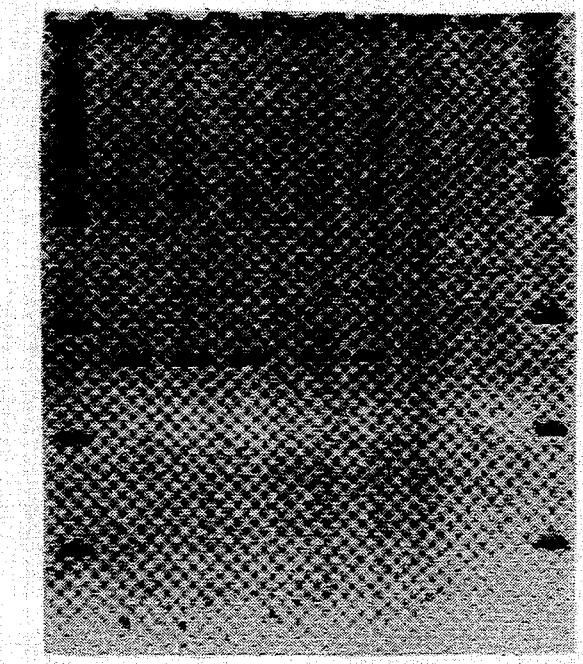

In FIG. 9E, primers 33-17-9 and 33-17-12a were omitted from the mix added after the first stage. Then, the second stage was performed with an 8 minute annealing time, rather than the usual 48 seconds. A faint band was visible in sample 5. Comparing this to the first stage only, a factor of 1000 additional 33-17-3, 33-17-6 primer product was made in the second stage. This proves that the first stage primers were not depleted after the first stage, a condition of the invention. Also, it proves the importance of reducing the annealing time in the kinetically controlled nesting.

EXAMPLE 2

In this case, the outer primers were 33-17-1.5 and 3-17-5.8, and the nested set was 33-17-3 and 33-17-6. Salmonella genomic DNA was the template.

The nesting parameters were:

First stage outer primer concentration, $P_{011} = 0.013$ μM

Second stage inner primer concentration, $P_{022} = 0.11$ μM

First stage annealing time, $t_1 = 8$ minutes
Second stage annealing time, $t_2 = 0.8$ minutes
First stage reaction volume, $V_1 = 25$ μl
Second stage reaction volume, $V_2 = 50$ μl
Number of cycles in first stage, $N_1 = 20$ Number of cycles in second stage, $N_2 = 20$ Using the kinetic parameter data from section F, the inequality constraints become:

| | (requirement) |
|---|---|
| $\epsilon_{max\ 1}(1-\exp(-k_1 P_{011} t_1)) = .68$ | $> 0.4$ |
| $\epsilon_{max\ 2}(1-\exp(-k_2 P_{022} t_2)) = .81$ | $> 0.4$ |
| $\epsilon_{max\ 1}(1-\exp(-k_1 P_{012} t_2)) = 0.06$ | $< (1/5)\epsilon_{max\ 2}$ $(1-\exp(-k_2 P_{022} t_2))$ |
| $k_1 P_{011} t_1 = 1.4$ | $1.2 < k_1 P_{011} t_1 < 2.3$ |
| $k_2 P_{022} t_2 = 2.4$ | $1.2 < k_2 P_{022} t_2$ |
| $V_2 t_1 / V_1 t_2 = 20$ | $15 < V_2 t_1 / V_1 t_2$ |
| $V_2 / V_1 = 2$ | $2 < V_2 / V_1 < 4$ |

Figure 10A:
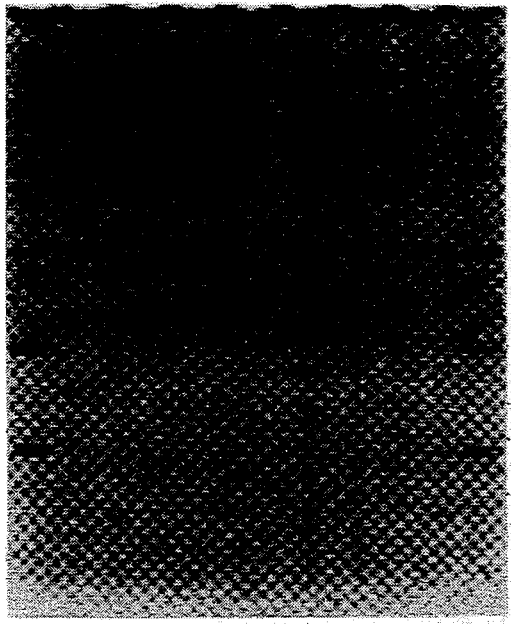
FIGS. 10A-10E demonstrates the kinetically controlled nesting with outer primers 33-17-1.5 and 33-17-5.8 and inner primers 33-17-3 and 33-17-6 using the Salmonella DNA samples described in FIG. 1. Shown are the results of each stage separately, the two stages combined, and the first stage done twice in sequence.

In FIG. 10A, Salmonella samples 1–7 were amplified in the first stage only. A faint band visible in sample 3 indicates an amplification factor of 150,000, and a per cycle efficiency of 0.81, above the minimum required 0.4. The model predicted an efficiency of 0.68.

Figure 10B:
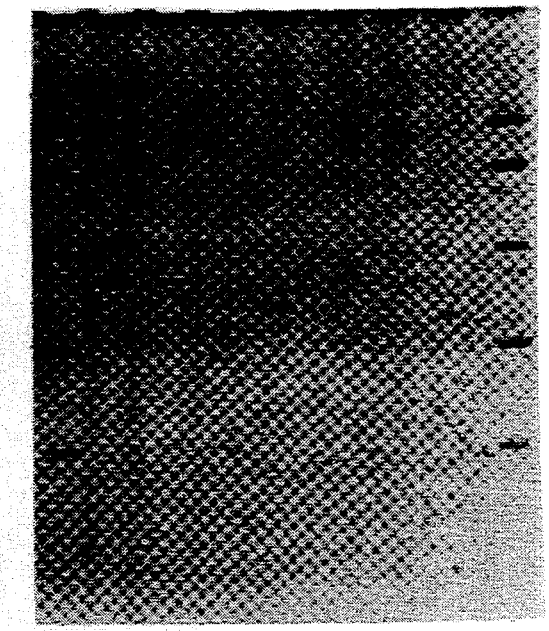
Figure 10C:
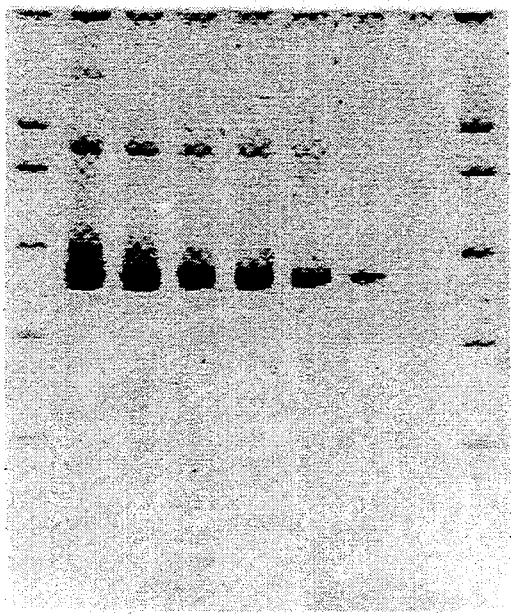

In FIG. 10B, the product of the second stage only is shown. The first stage was carried out in the same manner as in FIG. 10A, only the Taq polymerase was omitted. Prior to the second stage, 25 ul of 0.22 µM of primers 33-17-3 and 33-17-6 and Taq polymerase were added. In this case also, a faint 3,6 primer product is seen in Salmonella sample 3, indicating a 150,000 amplification factor and an efficiency of 0.81, identical to the model prediction.

Figure 10D:
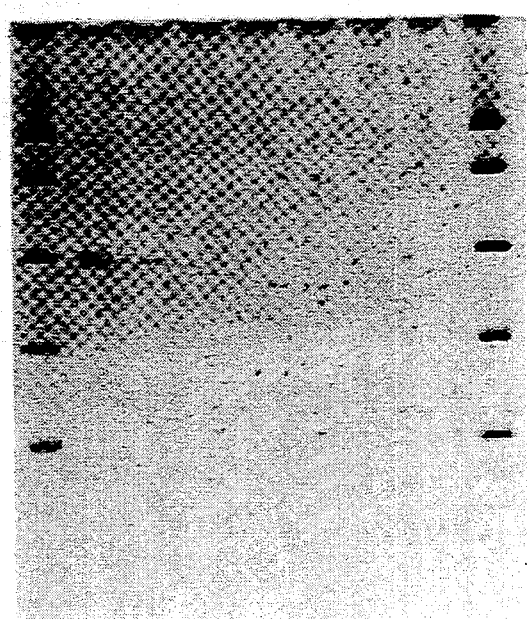

FIG. 10D shows the product of both stages with a bright 33-17-3 and 33-17-6 band in sample 6 and an overall amplification factor of greater than $10^8$.

In FIG. 10D, primers 33-17-3 and 33-17-6 were omitted from the second stage mix. A faint 1.5, 5.8 band in sample dilution 2 indicates that little or no additional product was made in the second stage, as desired and predicted by the model.

Figure 10E:
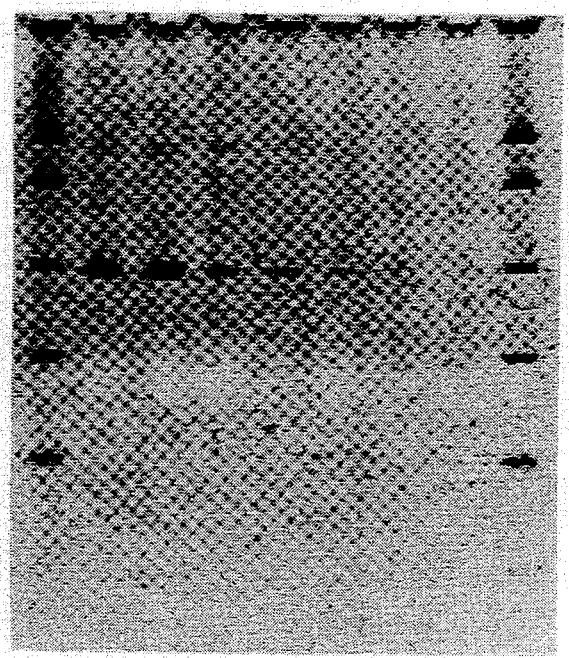

Finally, in FIG. 10E, the second stage primers were omitted from the second mix and the second stage annealing time was 8 minutes instead of 48 seconds. Clearly, the additional amplification product in the second stage proves that the primer was not depleted after the first stage.

EXAMPLE 3

In this example primers 15-G and 15-Y were nested within primers 15-A2 and 15-L. *E. coli* genomic DNA was the template.

The nesting parameters were:

First stage outer primer concentration, $P_{011} = 0.0053$ µM

Second stage inner primer concentration, $P_{022} = 0.27$ µM

First stage annealing time, $t_1 = 8$ minutes

Second stage annealing time, $t_2 = 0.8$ minutes

First stage reaction volume, $V_1 = 25$ µl

Second stage reaction volume, $V_2 = 50$ µl

Number of cycles in first stage, $N_1 = 18$

Number of cycles in second stage, $N_2 = 18$

Using the kinetic parameter data from section F, the inequality constraints become:

| | (requirement) |
|---|---|
| $\epsilon_{max\ 1}(1-\exp(-k_1 P_{011} t_1)) = .65$ | $> 0.4$ |
| $\epsilon_{max\ 1}(1-\exp(-k_1 P_{012} t_2)) = 0.06$ | $< (1/5)\epsilon_{max\ 2}$ $(1-\exp(-k_2 P_{022} t_2))$ |
| $k_1 P_{011} t_1 = 1.52$ | $1.2 < k_1 P_{011} t_1 < 2.3$ |
| $V_2 t_1 / V_1 t_2 = 20$ | $15 < V_2 t_1 / V_1 t_2$ |
| $V_2 / V_1 = 2$ | $2 < V_2 / V_1 < 4$ |

Some of the inequalities are omitted because the kinetic parameters were not measured for primers 15-G and 15-Y. Instead, the general recommendation of $P_{022}$ between 0.1 and 1 µM was used.

Figure 11A:
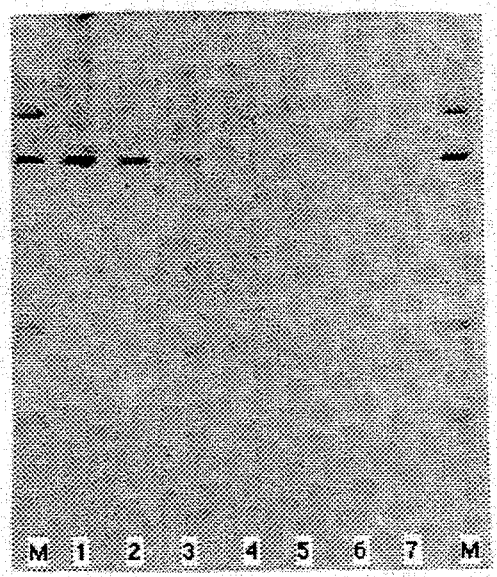
FIGS. 11A-11E demonstrates the kinetically controlled nesting with outer primers 15-A2 and 15-L and inner primers 15-G and 15-Y using the *E. coli* DNA samples described in FIG. 2. Shown are the results of each stage separately, the two stages combined, and the first stage done twice in sequence.

In FIG. 11A, *E. coli* samples 1–7 were amplified in the first stage only. A faint band was seen in sample 4, indicating an amplification factor of 120,000. The per cycle efficiency was 0.91, compared to 0.65 predicted by the model.

Figure 11B:
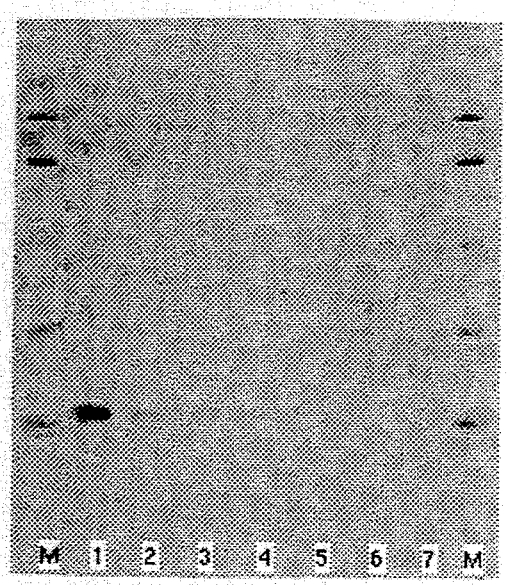

The second stage only is shown in FIG. 11B. Both the first and second stage protocols were followed, only Taq was eliminated from the first stage. FIG. 11B shows a faint band in sample 4, with an amplification factor of about 120,000 and a per stage efficiency of 0.91.

Figure 11C:
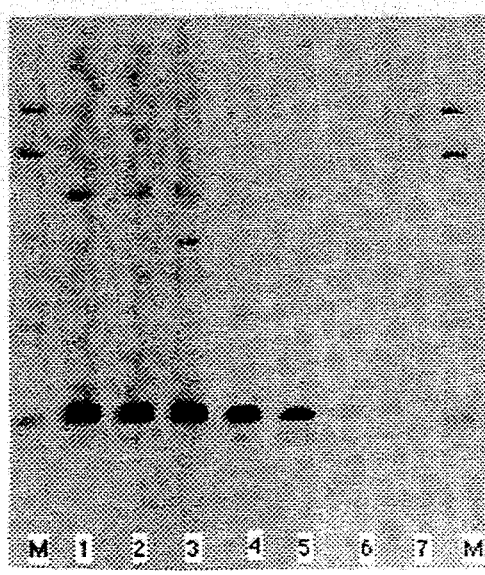

The first and second stages of amplification with Taq present in both stages is shown in FIG. 11C. A 15-G, 15-Y band in sample 6 demonstrated an amplification factor of greater than $1.2 \times 10^7$.

Figure 11D:
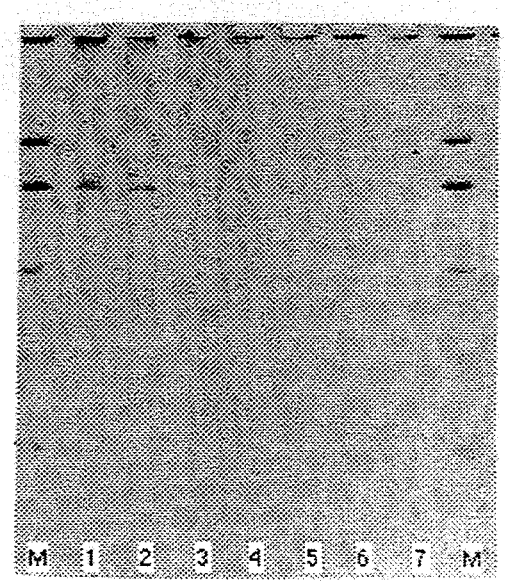

In FIG. 11D, the first and second stages were carried out omitting primers 15-G and 15-Y from the second stage mix. Comparing this output to the first stage only, little or no additional DNA was amplified by primers 15-A2 and 15-L in the second stage.

Figure 11E:
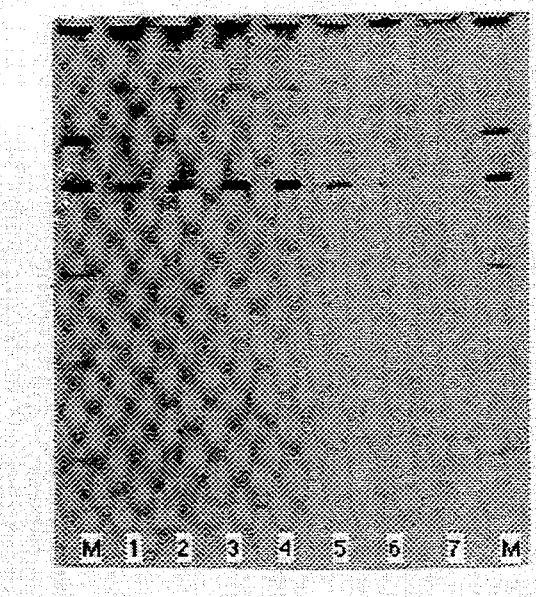

Finally, in FIG. 11E, 15-G and 15-Y were omitted from the second stage mix and the second stage annealing time was increased to 8 minutes. A significant amount of 15-A2, 15-L product was generated in the modified second stage, proving that the primers were not depleted after the first stage.

EXAMPLE 4

In this example, the nesting strategy of this invention was applied to the detection of Salmonella in food homogenates. Annealing kinetic parameters $\epsilon_{max} = 0.85$ and $k = 12.8$ (µM−min)$^{-1}$ were obtained for 23 mer outer primers 33-23-1.5 and 33-23-5.8 (Table 2). The inner primers 33-23-3 and 33-23-6.1 had kinetic parameters $\epsilon_{max} = 0.82$ and $k = 20.5$ (µM−min)$^{-1}$.

Raw ground beef, nonfat dry milk, cheddar cheese, soy flour, and ground black pepper were homogenized 10% w/v in lactose broth in a stomacher blender. *Salmonella typhimurium*, *Salmonella infantis*, and *Salmonella enteritidis* were spiked into the food homogenates at $10^7$, $10^6$, $10^5$, and $10^4$ viable counts per milliliter. A fifth sample in each series was the food homogenate with no added Salmonella.

DNA from the spiked homogenates was extracted according to the methods of section C above.

1 ul of the DNA extract was added to 24 ul of the first stage reaction mix. The nesting parameters were:

First stage outer primer concentration, $P_{011} = 0.031$ µM

Second stage inner primer concentration, $P_{022} = 0.17$ µM

First stage annealing time, $t_1 = 4$ minutes

Second stage annealing time, $t_2 = 0.67$ minutes

First stage reaction volume, $V_1 = 25$ µl

Second stage reaction volume, $V_2 = 75$ µl

Number of cycles in first stage, $N_1 = 23$

Number of cycles in second stage, $N_2 = 23$

|  | (requirement) |
|---|---|
| $\epsilon_{max\,1}(1-\exp(-(k_1 P_{011} t_1)) = .68$ | $>0.4$ |
| $\epsilon_{max\,2}(1-\exp(-(k_2 P_{022} t_2)) = .74$ | $>0.4$ |
| $\epsilon_{max\,1}(1-\exp(-(k_1 P_{012} t_2)) = 0.02$ | $<(1/5)\epsilon_{max\,2}(1-\exp(-(k_2 P_{022} t_2))$ |
| $k_1 P_{011} t_1 = 1.6$ | $1.2 < k_1 P_{011} t_1 < 2.3$ |
| $k_2 P_{022} t_2 = 2.3$ | $1.2 < k_2 P_{022} t_2$ |
| $V_2 t_1/V_1 t_2 = 24$ | $15 < V_2 t_1/V_1 t_2$ |
| $V_2/V_1 = 4$ | $2 < V_2/V_1 < 4$ |

Figure 12A:
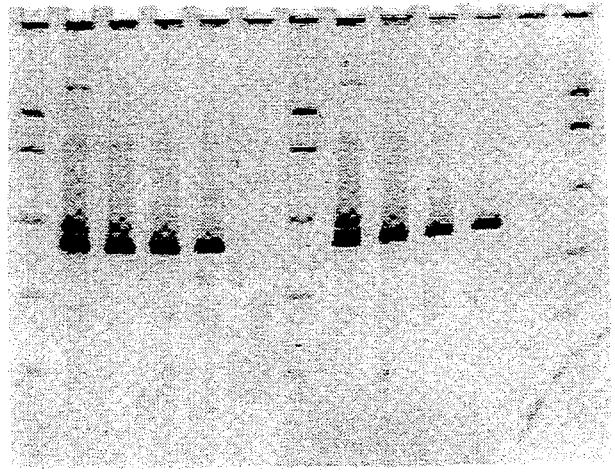
FIGS. 12A-12C shows the results of the kinetically controlled nesting applied to the food samples in listed in Table 6. The outer primer pair was 33-23-1.5 and 33-23-5.8 and the inner pair was 33-23-3 and 33-23-6.
Figure 12B:
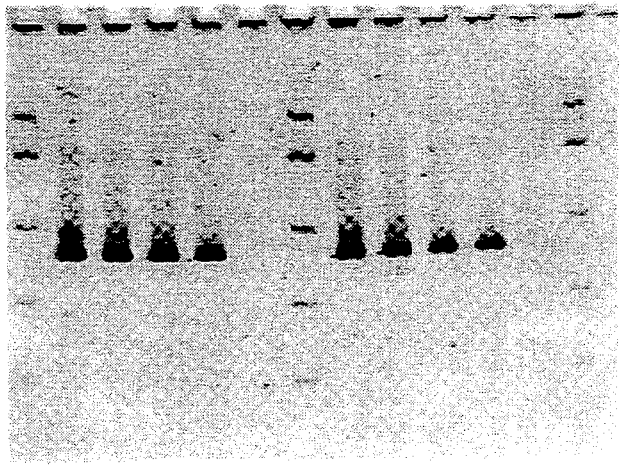
Figure 12C:
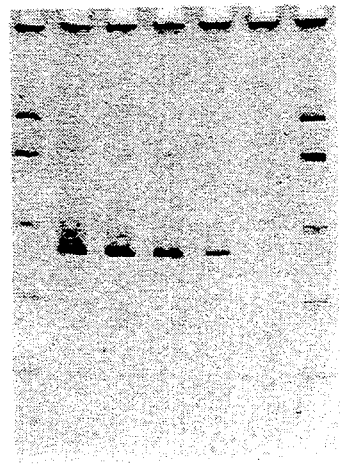
Figure 13A:
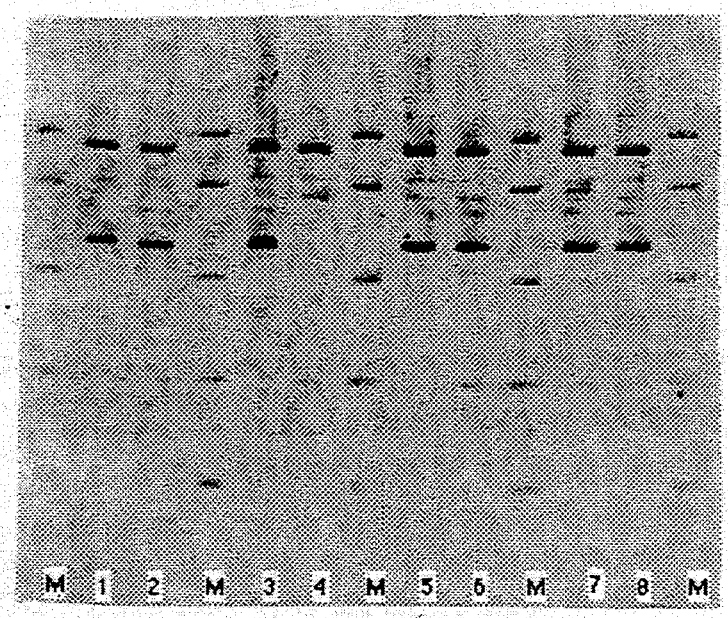
FIGS. 13A-13D shows the RAPD patterns obtained by the amplification of a panel of Salmonella genomic DNA with the arbitrary 12-mer primer CN03.
Figure 13B:
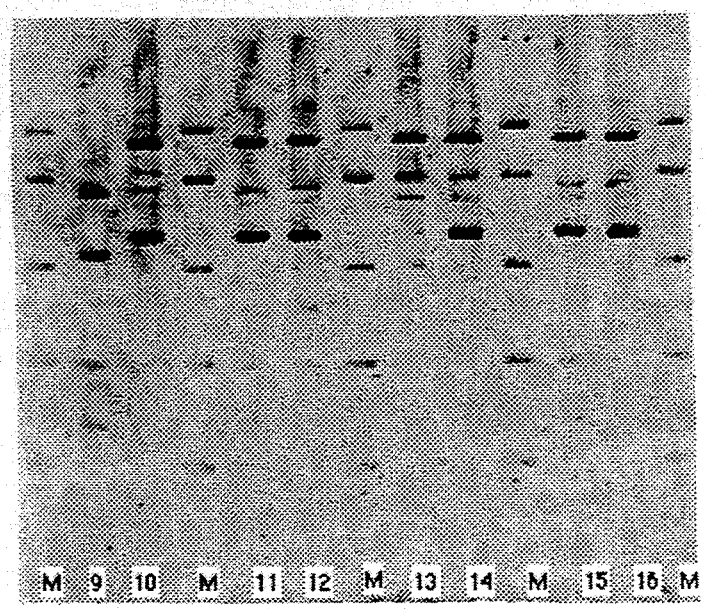
Figure 13C:
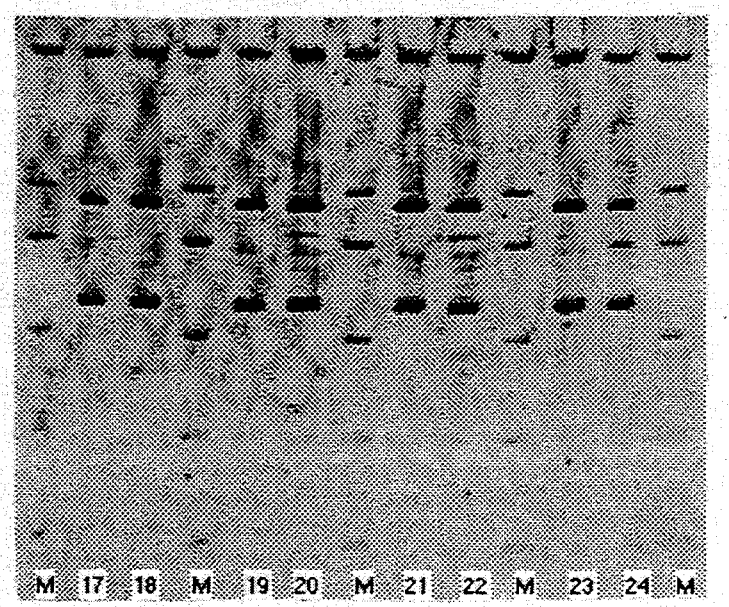
Figure 13D:
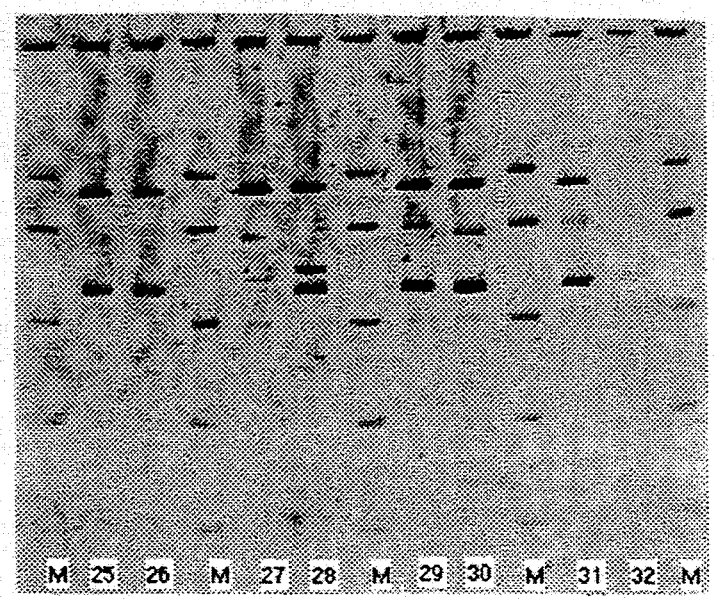
Figure 14A:
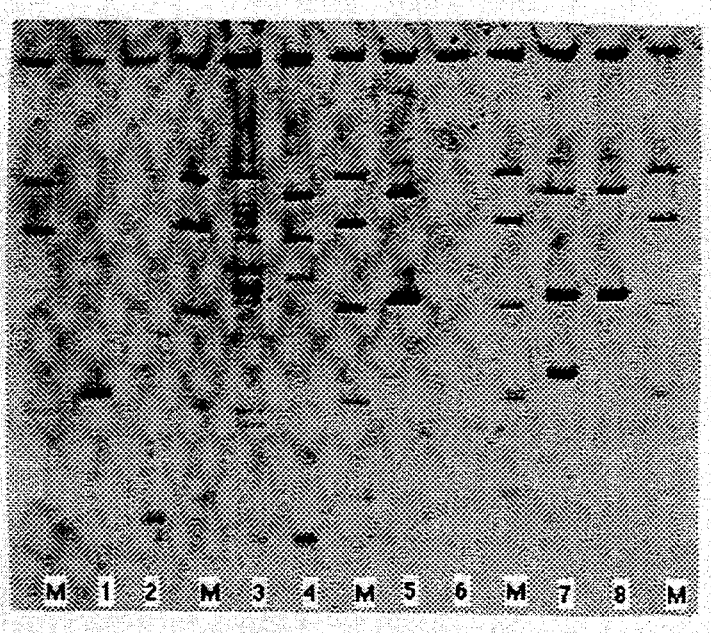
FIGS. 14A-14D shows the RAPD patterns obtained by the amplification of a panel of non-Salmonella genomic DNA with the arbitrary 12-mer primer CN03.
Figure 14B:
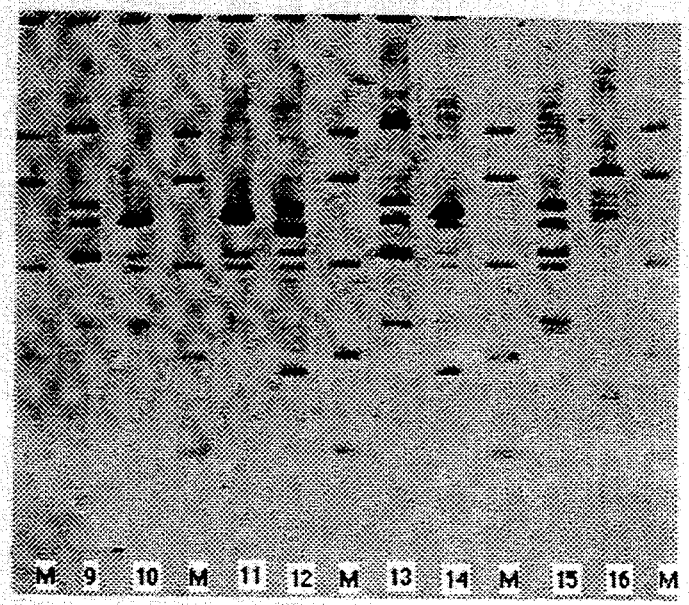
Figure 14C:
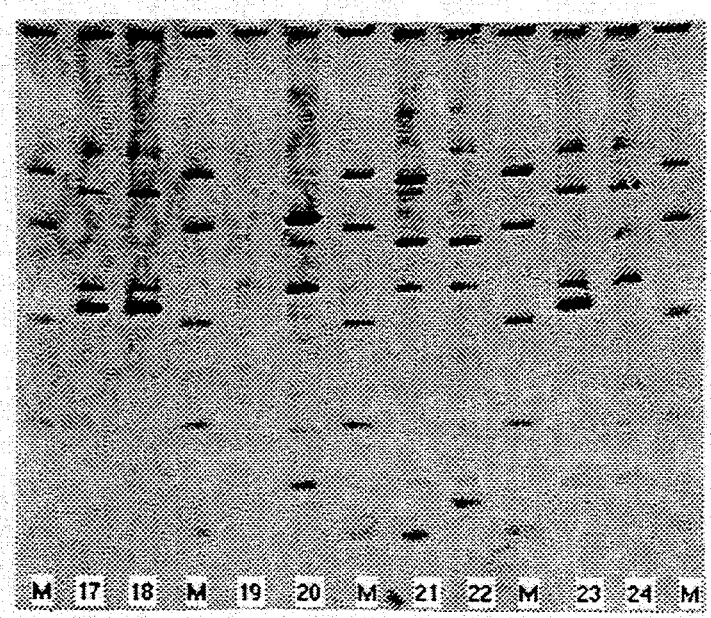
Figure 14D:
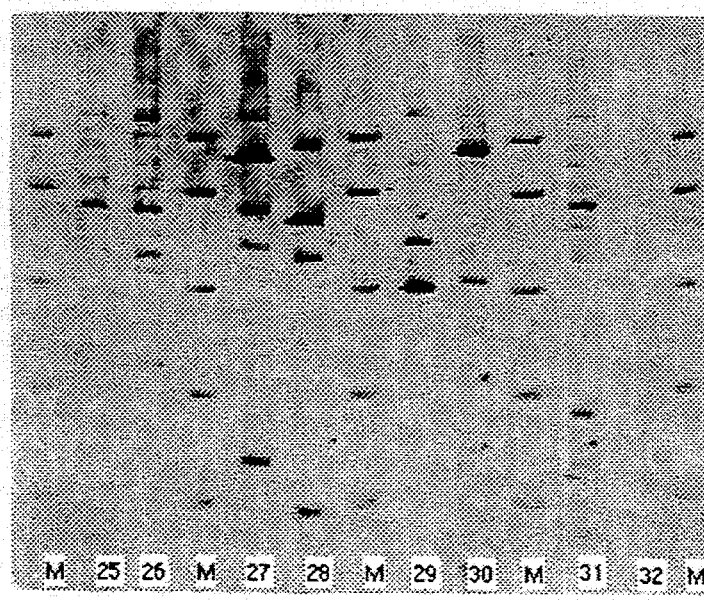

TABLE 6
Sample Identities of Lanes in FIG. 12

| Lane No. | Food | Salmonella sp. | Target DNA Copies Present |
|---|---|---|---|
| 1 | Ground Beef | *typhimurium* | 1E + 04 |
| 2 | Ground Beef | *typhimurium* | 1E + 03 |
| 3 | Ground Beef | *typhimurium* | 1E + 02 |
| 4 | Ground Beef | *typhimurium* | 1E + 01 |
| 5 | Ground Beef | *typhimurium* | 0E + 00 |
| 6 | Nonfat Dry Milk | *typhimurium* | 1E + 04 |

TABLE 6-continued
Sample Identities of Lanes in FIG. 12

| Lane No. | Food | Salmonella sp. | Target DNA Copies Present |
|---|---|---|---|
| 7 | Nonfat Dry Milk | *typhimurium* | 1E + 03 |
| 8 | Nonfat Dry Milk | *typhimurium* | 1E + 02 |
| 9 | Nonfat Dry Milk | *typhimurium* | 1E + 01 |
| 10 | Nonfat Dry Milk | *typhimurium* | 0E + 00 |
| 11 | Cheddar Cheese | *enteritidis* | 1E + 04 |
| 12 | Cheddar Cheese | *enteritidis* | 1E + 03 |
| 13 | Cheddar Cheese | *enteritidis* | 1E + 02 |
| 14 | Cheddar Cheese | *enteritidis* | 1E + 01 |
| 15 | Cheddar Cheese | *enteritidis* | 0E + 00 |
| 16 | Soy Flour | *enteritidis* | 1E + 04 |
| 17 | Soy Flour | *enteritidis* | 1E + 03 |
| 18 | Soy Flour | *enteritidis* | 1E + 02 |
| 19 | Soy Flour | *enteritidis* | 1E + 01 |
| 20 | Soy Flour | *enteritidis* | 0E + 00 |
| 21 | Black Pepper | *infantis* | 1E + 04 |
| 22 | Black Pepper | *infantis* | 1E + 03 |
| 23 | Black Pepper | *infantis* | 1E + 02 |
| 24 | Black Pepper | *infantis* | 1E + 01 |
| 25 | Black Pepper | *infantis* | 0E + 00 |

We claim:

1. An improved method for performing a nested polymerase chain reaction to selectively amplify a target segment of nucleic acid from a sample nucleic acid reaction mixture, said method amplifying in the first stage a nucleic acid segment flanked by an outer primer pair and in the second stage a nucleic acid target segment flanked by an inner nested primer pair; the improvement comprising wherein by controlling the concentrations and annealing times of the outer and inner primer pairs in the first and second stages selective amplification of the target segment is accomplished during the second stage by the inner primer pair, wherein the entire volume of the first stage reaction mixture is used in the second stage without depletion or removal of the outer primers from the reaction mixture; the improved method comprises the steps of:

adding a pair of outer primers to a sample nucleic acid reaction mixture to achieve a concentration of said outer primers which is described by $P_{011}$;

repetitively performing the polymerase chain reaction utilizing an annealing time at each cycle which is described by $t_1$;

adding a pair of inner primers to the sample nucleic acid reaction mixture to achieve a concentration of said inner primer which is described by $P_{022}$; and repetitively performing the polymerase chain reaction utilizing an annealing time at each cycle which is described by $t_2$; wherein $P_{011}$, $t_1$, $P_{022}$ and $t_2$ are selected according to the formulas $$\epsilon_{max\,1}(1-\exp-(k_1 P_{011} t_1)) > 0.4$$

$$\epsilon_{max\,2}(1-\exp-(k_2 P_{022} t_2)) > 0.4$$

$$\epsilon_{max\,1}(1-\exp(-k_1 P_{012} t_2)) < 1/5\,\epsilon_{max\,2}(1-\exp(-k_2 P_{022} t_2))$$

wherein $P_{011}$ is the concentration of each of the outer primers in the first stage;

$P_{022}$ is the concentration of each of the inner primers in the second stage;

$P_{012}$ is the concentration of each of the outer primers in the second stage;

$t_1$ is the annealing time in the first stage;

$t_2$ is the annealing time in the second stage;

$k_1$ is the second order rate constant for the formation of extension product from the outer primers;

$k_2$ is the second order rate constant for the formation of extension product from the inner primers;

$\epsilon_{max\,1}$ is the maximum per cycle primer extension of the outer primer; and $\epsilon_{max\,2}$ is the maximum per cycle extension of the inner primers.

2. The method of claim 1 wherein the first and second stage primer concentrations and annealing time values are as follows:

$$1.2 < k_1 P_{011} t_1 < 2.3,$$

$$1.2 < k_2 P_{022} t_2 < 2.3,$$

$$15 < V_2 t_1 / V_1 t_2 < 20, \text{ and}$$

$$2 < V_2/V_1 < 4$$

wherein $V_1$ is the total reactant volume in the first stage of amplification, $V_2$ is the total reactant volume in the second stage, and $V_2 - V_1$ is the volume in which the inner primers are added after the first stage and prior to the second stage.

3. The method of claim 1 wherein:

for $1 < V_2/V_1 < 2$;

$t_1$ is 6.5 to 13 minutes, $P_{011}$ is 0.0015–0.03 micromolar, $t_2$ is 0.5–1.6 minutes, and $P_{022}$ is 0.1–1 micromolar, wherein $V_1$ is the total reactant volume in the first stage of amplification, $V_2$ is the total reactant volume in the second stage, and $V_2-V_1$ is the volume in which the inner primers are added after the first stage and prior to the second stage.

4. The method of claim 1 wherein:
for $2<V_2/V_1<3$;
$t_1$ is 4 to 9 minutes,
$P_{011}$ is 0.0025–0.05 micromolar,
$t_2$ is 0.5–1.6 minutes, and
$P_{022}$ is 0.1–1 micromolar,
wherein $V_1$ is the total reactant volume in the first stage of amplification, $V_2$ is the total reactant volume in the second stage, and $V_2-V_1$ is the volume in which the inner primers are added after the first stage and prior to the second stage.

5. The method of claim 1 wherein:
for $3<V_2/V_1<4$;
$t_1$ is 2.5 to 6.5 minutes,
$P_{011}$ is 0.0035–0.07 micromolar,
$t_2$ is 0.5–1.6 minutes, and
$P_{022}$ is 0.1–1 micromolar,
wherein $V_1$ is the total reactant volume in the first stage of amplification, $V_2$ is the total reactant volume in the second stage, and $V_2-V_1$ is the volume in which the inner primers are added after the first stage and prior to the second stage.

6. The method of claim 1 wherein the target segment of nucleic acid is comprised of DNA.

7. The method of claim 6 wherein the target segment of nucleic acid is comprised of DNA known to be diagnostic to a particular genus, species or subspecies of microorganism.

8. The method of claim 7 wherein the sample nucleic acid reaction mixture is comprised of DNA extracted from microorganisms of undetermined identity.

9. The method of claim 7 wherein the diagnostic target segment of DNA of a particular genus, species or subspecies of microorganism has been determined by generating a series of random polymorphic markers using single primer random amplified polymorphic analyses and then identifying and selecting a unique marker among those markers generated.

10. The method of claim 8 further comprising a final step of detecting the presence of the selectively amplified target segment of DNA whereby the presence of a particular genus, species or subspecies of microorganism in the sample nucleic acid mixture is determined.

11. The method of claim 10 wherein the sample nucleic acid mixture comprises DNA extracted from microorganisms derived from or contained within food samples.

12. The method of claim 11 wherein the particular genus, species or subspecies of microorganism is selected from the group consisting of: the genus Salmonella; a subgroup of the genus Salmonella; and the species *Escherichia coli*.

13. The method of claim 1 wherein the sample nucleic acid reaction mixture contains nucleic acids extracted from microorganisms derived from or contained within environmental samples.

14. The method of claim 1 wherein the sample nucleic acid reaction mixture contains nucleic acids extracted from cells derived from or contained within human or animal biological samples.

15. The method of claim 12 wherein the particular microorganism belongs to the genus Salmonella.

16. The method of claim 15 wherein the outer or inner primers used to achieve amplification of the Salmonella target nucleic acid have nucleic acid sequences selected from the group consisting of:
5'(GAC GCT TAA TGC GGT TAA CGC CA)3' SEQ ID NO.:9,
5'(TCA GGA TGC AGG CGA TAG TAG CC)3' SEQ ID NO.:10,
5'(AAC CAT GCA TCA TCG GCA GAA CG)3' SEQ ID NO.:11,
5'(AGG CGA TAG TAG CCT GCC GCT TA)3' SEQ ID NO.:12,
5'(AAC CAT GCA TCA TCG GC)3' SEQ ID NO.:13,
5'(TAG TAG CCT GCC GCT TA)3' SEQ ID NO.:14,
5'(GGA CGC TTA ATG CGG TT)3' SEQ ID NO.:15,
5'(ATT CAG GAT GCA GGC GA)3' SEQ ID NO.:16,
5'(GGC TAA TCC AAG GGC AA)3' SEQ ID NO.:17 and
5'(TAT GAC CGT CCT CTC CT)3' SEQ ID NO.:18.

SEQ ID NO.: 9
5'(GAC GCT TAA TGC GGT TAA CGC CA)3',
SEQ ID NO.: 10
5'(TCA GGA TGC AGG CGA TAG TAG CC)3',
SEQ ID NO.: 11
5'(AAC CAT GCA TCA TCG GCA GAA CG)3',
SEQ ID NO.: 12
5'(AGG CGA TAG TAG CCT GCC GCT TA)3',
SEQ ID NO.: 13
5'(AAC CAT GCA GCA TCA TCG GC)3',
SEQ ID NO.: 14
5'(TAG TAG CCT GCC GCT TA)3',
SEQ ID NO.: 15
5'(GGA CGC TTA ATG CGG TT)3',
SEQ ID NO.: 16
5'(ATT CAG GAT GCA GGC GA)3',
SEQ ID NO.: 17
5'(GGC TAA TCC AAG GGC AA)3',
and
SEQ ID NO.: 18
5'(TAT GAC CGT CCT CTC CT)3'.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGCTGATGCT AC                                  12

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGTCGAACTG TC                                  12

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TTAGTCACGG CA                                  12

( 2 ) INFORMATION FOR SEQ ID NO:4:

( i ) SEQUENCE CHARACTERISTICS:

(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TGCGATACCG TA                                                            12

(2) INFORMATION FOR SEQ ID NO:5:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

CTACAGCTGA TG                                                            12

(2) INFORMATION FOR SEQ ID NO:6:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

GTCAGTCGAA CT                                                            12

(2) INFORMATION FOR SEQ ID NO:7:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

GGCATTAGTC AC                                                            12

(2) INFORMATION FOR SEQ ID NO:8:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

CGTATGCGAT AC                                                            12

(2) INFORMATION FOR SEQ ID NO:9:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

( x i ) SEQUENCE DESCRIPTION: SEQ ID NO:9:

GACGCTTAAT GCGGTTAACG CCA					23

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TCAGGATGCA GGCGATAGTA GCC					23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AACCATGCAT CATCGGCAGA ACG					23

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AGGCGATAGT AGCCTGCCGC TTA					23

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AACCATGCAT CATCGGC					17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TAGTAGCCTG CCGCTTA					17

( 2 ) INFORMATION FOR SEQ ID NO:15:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

GGACGCTTAA TGCGGTT           17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ATTCAGGATG CAGGCGA           17

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGCTAATCCA AGGGCAA           17

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TATGACCGTC CTCTCCT           17

( 2 ) INFORMATION FOR SEQ ID NO:19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TAGCGGTGAA ATGCG           15

( 2 ) INFORMATION FOR SEQ ID NO:20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:20:

CAAGGCATCC ACCGT                                                                                          15

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:21:

GAAGTCGTAA CAAGG                                                                                          15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:22:

TCCTGGGCCT CTAGA                                                                                          15